United States Patent
Sun

(10) Patent No.: US 10,850,007 B2
(45) Date of Patent: *Dec. 1, 2020

(54) ELASTASE TREATMENT OF TISSUE MATRICES

(71) Applicant: LifeCell Corporation, Madison, NJ (US)

(72) Inventor: Wendell Sun, Warrington, PA (US)

(73) Assignee: LifeCell Corporation, Madison, NJ (US)

( * ) Notice: Subject to any disclaimer, the term of this patent is extended or adjusted under 35 U.S.C. 154(b) by 176 days.

This patent is subject to a terminal disclaimer.

(21) Appl. No.: 16/028,870

(22) Filed: Jul. 6, 2018

(65) Prior Publication Data

US 2018/0311410 A1 Nov. 1, 2018

Related U.S. Application Data

(63) Continuation of application No. 14/989,301, filed on Jan. 6, 2016, now Pat. No. 10,022,473, which is a continuation of application No. 12/478,435, filed on Jun. 4, 2009, now Pat. No. 9,259,511.

(60) Provisional application No. 61/059,604, filed on Jun. 6, 2008.

(51) Int. Cl.
*A61L 27/36* (2006.01)
*F01C 21/06* (2006.01)
*F03C 2/08* (2006.01)

(52) U.S. Cl.
CPC ......... *A61L 27/3687* (2013.01); *A61L 27/362* (2013.01); *A61L 27/3604* (2013.01); *F01C 21/06* (2013.01); *F03C 2/08* (2013.01)

(58) Field of Classification Search
CPC ............... A61L 27/3604; A61L 27/362; A61L 27/3687; F01C 1/06; F03C 2/08
See application file for complete search history.

(56) References Cited

U.S. PATENT DOCUMENTS

| | | | |
|---|---|---|---|
| 5,336,616 A | 8/1994 | Livesey et al. | |
| 5,364,756 A | 11/1994 | Livesey et al. | |
| 6,381,026 B1 | 4/2002 | Schiff et al. | |
| 6,933,326 B1 | 8/2005 | Griffey et al. | |
| 7,358,284 B2 | 4/2008 | Griffey et al. | |
| 9,259,511 B2 * | 2/2016 | Sun | F03C 2/08 |
| 10,022,473 B2 | 7/2018 | Sun | |
| 2003/0035843 A1 | 2/2003 | Livesey et al. | |

(Continued)

FOREIGN PATENT DOCUMENTS

WO 2007/043513 A1 4/2007

OTHER PUBLICATIONS

Dobrin et al., Elastase, collagenase, and the biaxial elastic properties of dog carotid artery. Am J Physiol. Jul. 1984;247(1 Pt 2):H124-31.

(Continued)

*Primary Examiner* — Jocelin C Tanner
(74) *Attorney, Agent, or Firm* — McCarter & English, LLP

(57) ABSTRACT

A method of producing a modified acellular tissue matrix (mATM) from an acellular tissue matrix (ATM), where the mATM has a reduced stretchiness relative to the ATM, without substantially compromising its associated structural or functional integrity. The method includes providing an acellular tissue matrix (ATM) and exposing the ATM to elastase for a period of time.

15 Claims, 11 Drawing Sheets

(56) References Cited

U.S. PATENT DOCUMENTS

| | | |
|---|---|---|
| 2003/0143207 A1* | 7/2003 | Livesey .......... A61L 27/54 424/93.7 |
| 2005/0028228 A1 | 2/2005 | McQuillan et al. |
| 2006/0073592 A1 | 4/2006 | Sun et al. |
| 2006/0127375 A1 | 6/2006 | Livesey et al. |
| 2006/0210960 A1 | 9/2006 | Livesey et al. |
| 2007/0009586 A1 | 1/2007 | Cohen et al. |
| 2007/0248575 A1 | 10/2007 | Connor et al. |
| 2008/0027562 A1 | 1/2008 | Fujisato et al. |
| 2009/0130221 A1 | 5/2009 | Bolland et al. |

OTHER PUBLICATIONS

Karlinsky et al., In vitro effects of elastase and collagenase on mechanical properties of hamster lungs. Chest. Feb. 1976;69(2 Suppl):275-6.

Lu et al., Novel porous aortic elastin and collagen scaffolds for tissue engineering. Biomaterials. Oct. 2004;25(22):5227-37.

Reihsner et al., Biomechanical properties of elastase treated palmar aponeuroses. Connect Tissue Res. 1991;26(1-2):77-86.

Tedder et al., Stabilized collagen scaffolds for heart valve tissue engineering. Tissue Eng Part A. Jun. 2009;15(6):1257-68.

Yuan et al., Effects of collagenase and elastase on the mechanical properties of lung tissue strips. J Appl Physiol (1985). Jul. 2000;89(1):3-14.

International Search Report and Written Opinion for Application No. PCT/US2009/046193, dated Jul. 30, 2010. 12 pages.

\* cited by examiner

ELASTASE TREATMENT OF TISSUE MATRICES

This application is a continuation application of U.S. patent application Ser. No. 14/989,301, filed on Jan. 6, 2016, which is a continuation application of U.S. Pat. No. 9,259,511 filed on Jun. 4, 2009, which claims priority under 35 U.S.C. § 119 to U.S. Provisional Patent Application No. 61/059,604, filed on Jun. 6, 2008. All related applications are herein incorporated by reference in their entirety.

FIELD

This disclosure relates to acellular tissue matrices (ATMs) for implanting or grafting to vertebrate subjects. More particularly, the disclosure relates to reducing stretchiness in ATMs and reducing variations in stretchiness across a group of ATMs without substantially affecting the structural or functional integrity of the ATMs.

BACKGROUND

Mechanical properties of implantable or graftable tissue can vary a great deal. Because of such variations, surgeons sometimes pre-stretch tissue matrices prior to implanting or grafting. Additionally, for repair of particularly large tissue defects, multiple pieces of tissue grafts may need to be sutured together. In those instances, variations in mechanical properties may complicate, for example, the suturing and implanting or grafting procedure.

SUMMARY

The present disclosure relates to reducing stretchiness in ATMs and reducing variations in stretchiness across a group of ATMs without substantially affecting the structural or functional integrity in the ATMs.

In one aspect, a method includes providing an acellular tissue matrix (ATM) and exposing the ATM to elastase for a period of time. For instance, an ATM may be exposed to a solution containing a concentration of elastase for a period of time. The exposure results in a modified ATM (mATM) that has a reduced stretchiness relative to the ATM. In other words, the percent extension (or strain) of the mATM resulting from a specific amount of tensile force is less than the percent extension (or strain) of ATM resulting from the same amount of tensile force. In some implementations, the exposure time and the concentration of elastase are controlled to obtain a desired stretchiness of the mATM. The desired stretchiness of the mATM may be such that, under an applied tensile force of about 5 newtons/cm, the percent extension of the mATM ranges between 14% to 24%. For example, the percent extension of the mATM under a tensile force of about 5 newtons/cm is about 19%. In some implementations, the elastase concentration is between about 0.1 units/milliliter and 0.5 units/milliliter or is between about 0.2 units/milliliter and 0.25 units/milliliter. The elastase exposure time typically is between about 12 and 24 hours and also typically is at least 18 hours. Certain embodiments of the method include agitating the ATM and the solution during exposure. Such agitation may be gentle or more intense. The agitation may be implemented by steadily shaking the container holding the tissue and elastase solution or by flipping the container over again and again. The shaking speed and amplitude may vary, as may the rate at which the container is flipped.

The ATM may be, for example, a tissue (e.g., a dermis) from which all, or substantially all, viable cells have been removed. The tissue may include, for example, fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and/or intestinal tissue. In some embodiments, the ATM may be made from human tissue, non-human mammalian tissue or porcine tissue. The non-human mammalian tissue may be bovine tissue.

Another aspect includes a modified acellular tissue matrix made by any of the foregoing methods.

According to yet another aspect, a method includes providing a group of acellular tissue matrices (ATMs), wherein when an equal amount of tensile force is applied to each of the ATMs in the group, at least some of the ATMs in the group have a different stretchiness (percent extension) than other ATMs in the group, exposing one or more of the ATMs to elastase for a period of time. The elastase may be in the form of a solution containing a concentration of elastase. In some embodiments, the elastase exposure results in one or more modified ATMs (mATMs). The one or more of the mATMs are less stretchy than their respective, corresponding ATMs. In some embodiments, the percent extension of the one or more of the mATMs resulting from an amount of tensile force is less than the percent extension of their corresponding ATMs resulting from the same amount of tensile force. In some implementations, the variations in stretchiness across the mATMs are less significant than the variations in stretchiness across the ATMs.

In some embodiments, the variation in stretchiness across the mATMs is such that, under a tensile force of about 5 newtons/cm, at least some of the mATMs extend between about 14% and 24%. In some embodiments, the variation in stretchiness across the mATMs is such that, under a tensile force of about 5 newtons/cm, a plurality of the mATMs extend about 19%.

Certain implementations include providing an elastase concentration between about 0.1 units/milliliter and 0.5 units/milliliter or between about 0.2 units/milliliter and 0.25 units/milliliter. The exposure time, typically, is between about 12 and 24 hours and, typically, is at least about 18 hours.

In some implementations, the one or more ATMs of the group are agitated when exposed to the solution.

The ATMs may include, for example, tissue (e.g., dermis) from which all, or substantially all viable cells have been removed. The tissue may include, for example, fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and/or intestinal tissue. The ATMs may be made from human tissue, non-human mammalian tissue (e.g., porcine tissue or bovine tissue).

Yet another aspect includes a group of modified acellular tissue matrices treated according to the forgoing method(s).

A further aspect includes a method including providing an acellular tissue matrix (ATM) and exposing the ATM to elastase for a period of time. Typically, the elastase is in a solution containing a concentration of elastase. The exposure results in a modified ATM (mATM) that has a reduced stretchiness relative to the ATM. The method further includes identifying a vertebrate subject as having an organ or tissue in need of repair or amelioration and placing the mATM (or more than one mATM sutured together) in or on the tissue or organ.

Still another aspect includes a method including providing a group of acellular tissue matrices (ATMs), where at least some of the ATMs in the group have a different stretchiness than other ATMs in the group and exposing one or more ATMs of the group to elastase (e.g., a solution containing a concentration of elastase) for a period of time, the exposure resulting in one or more modified ATMs (mATMs), wherein the one or more of the mATMs are less stretchy than their respective, corresponding ATMs. The method further includes identifying a vertebrate subject as having an organ or tissue in need of repair or amelioration and placing the mATM in or on the tissue or organ.

Moreover, another aspect includes a modified acellular tissue matrix (mATM) including an elastin network and a collagen matrix, wherein the elastin network has been disrupted so that the mATM's stretchiness is such that, under an applied tensile force of about 5 newtons/cm, the mATM extends between about 14% and 24% and wherein the collagen network is substantially intact. In certain implementations, the collagen network does not include cross-linking.

In a typical implementation, the tissue's elastin network is sufficiently disrupted so that the mATM's stretchiness is such that, under an applied tensile force of about 5 newtons/cm, the mATM extends between about 14% and 24% and the mATM's collagen network is substantially intact. In some embodiments, mATM's collagen network has substantially similar characteristics as the ATM's collagen network. For instance, the histological, thermal, and material properties of the mATM are similar to those of the ATM.

Tissues having excessive stretchiness may be treated to obtain tissues having only a particular desired level of stretchiness. Additionally, variations in stretchiness from tissue sample to tissue sample may be reduced. This may be particularly helpful in procedures that require joining more than one piece of tissue together in order to repair and/or ameliorate a tissue or organ. Uniformity of tissue sample stretchiness may be realized.

Unless otherwise defined, all technical and scientific terms used herein have the same meaning as commonly understood by one of ordinary skill in the art to which the present disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

Other features and advantages of the present disclosure will be apparent from the following description, from the drawings and from the claims.

DETAILED DESCRIPTION

The present disclosure relates to acellular tissue matrices (ATMs) that can be implanted in or grafted to, for example, vertebrate subjects. More particularly, this disclosure relates to producing modified ATMs (mATMs) having reduced stretchiness relative to their corresponding ATMs, without substantially compromising the associated structural or functional integrity of the tissue. Additionally, the disclosure relates to producing a group of mATMs from a group of ATMs, where the stretchiness of tissues in the group of mATMs has less variation than the stretchiness of tissues in the group of ATMs. In other words, the percent extension of tissues in the group of mATMs under a specific amount of tensile force has less variation than the percent extension of tissues in the group of ATMs under the same amount of tensile force.

Figure 1:
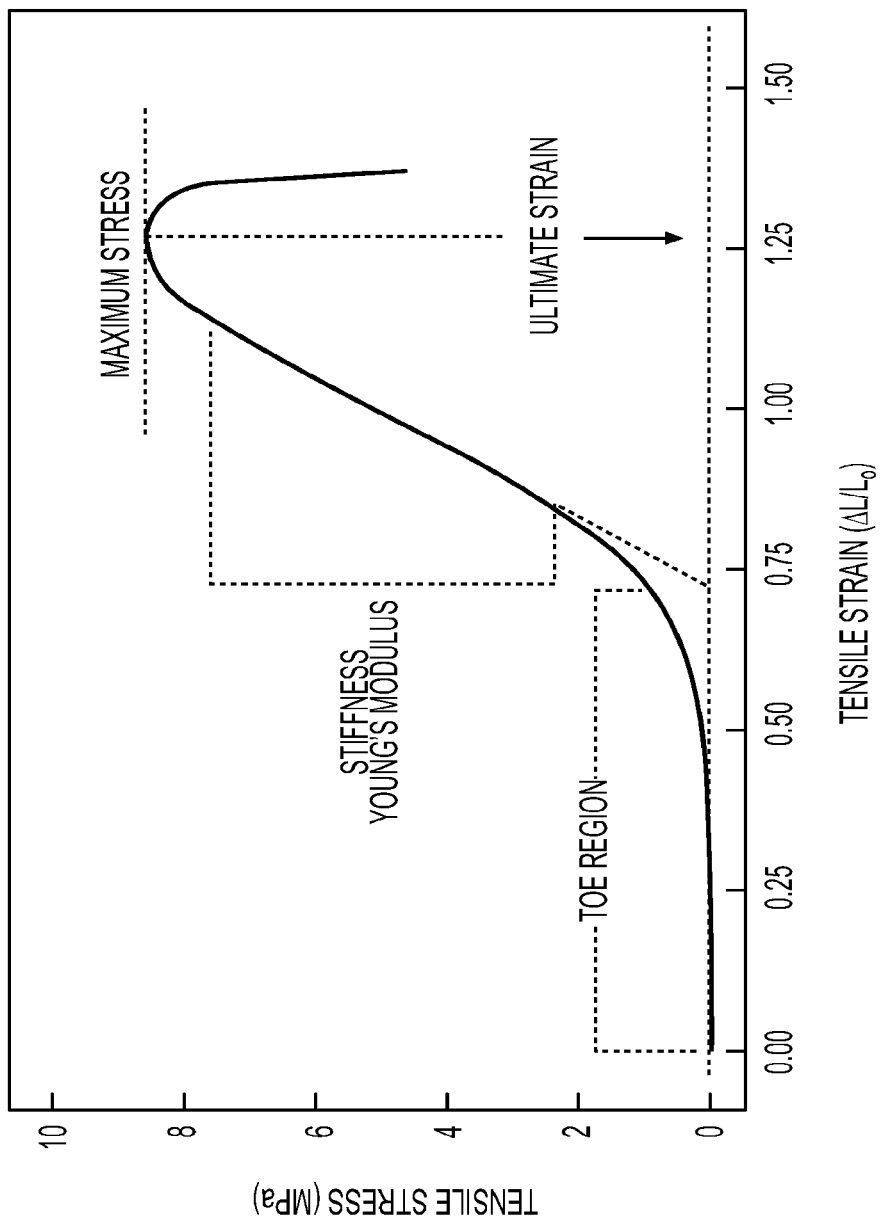
FIG. 1 is a line graph showing a stress-strain diagram of a typical fully hydrated tissue sample.

As used herein, the term "stretchiness" refers generally to the ability of tissue or a tissue matrix to stretch or expand under an applied tensile stress. FIG. 1 depicts a typical stress-strain curve for a fully hydrated dermis tissue matrix. The ordinate represents tensile stress in megapascals ("MPa") and the abscissa represents tensile strain. "Tensile stress" is defined as $S=F/A_o$, wherein F is the tensile force, and $A_o$ is the cross-sectional area of the test sample. "Tensile strain" is defined as $(L_f-L_o)/L_o$ (i.e. $\Delta L/L_o$), wherein $L_o$ is the original length of the tissue matrice, $L_f$ is the length of the tissue matrice under a tensile stress, and $\Delta L$ is the change in length that the tissue matrix experiences (i.e. $L_f-L_o=\Delta L$). In addition, as used herein, "percent extension" is defined as $(L_f-L_o)/L_o \times 100\%$ (i.e. $\Delta L/L_o \times 100\%$) and thus is used interchangeably with the term "tensile strain" throughout the speciation.

The indicated non-linear relationship, typical of many soft tissues, consists of three well-defined tensile response phases. The first phase is the toe region; the second phase corresponds to the extension of collagen fibrils under stress; and the last phase results from the yielding and final breaking of the tissue material. The stretchiness of tissue may be represented by the length of the toe region, which is determined by extrapolating the second phase of the curve to intercept the x-axis. This can be done mathematically using the linear equation y=a+bx. The x-axis intercept is −a/b.

Alternatively, the comparison between the tensile strain (or percent extension) of mATM and ATM under a small force of about 5 newtons/cm is provided as a method for comparing the stretchiness of mATM and ATM.

As used herein, a "fully hydrated" ATM or tissue is an ATM or tissue containing the maximum amount of bound and unbound water that it is possible for that ATM or tissue to contain under atmospheric pressure. In comparing the amounts of water (unbound and/or bound) in two or more ATMs that are fully hydrated, since the maximum amount of water of an ATM made from any particular tissue will vary with the temperature of the ATM, it is of course important that measurements for the two (or more) ATM be made at the same temperature. Examples of fully hydrated ATM include, without limitation, those at the end of the decellularizing process described in Example 1 and an ATM that has been rehydrated at room temperature (i.e., about 15° C. to about 35° C.) in 0.9% sodium chloride solution for 4 hours following a prior freeze-drying process such as those described herein. Bound water in an ATM is the water in the ATM whose molecular mobility (rotational and translational) is reduced (compared to pure bulky water) due to molecular interactions (e.g., hydrogen bonding) between the water and ATM molecules and/or other phenomena (e.g., surface tension and geometric restriction) that limit the mobility of the water in the ATM. Unbound water within the ATM has the same molecular mobility properties as bulky water in dilute aqueous solutions such as, for example, biological fluids. As used herein, a "partially hydrated ATM" is an ATM that contains, at atmospheric pressure, less than 100% but more than 30% (e.g., more than: 35%; 40%; 45%; 50%; 55%; 60%; 65%; 70%; 75%; 80%; 85%; 90%; 95%; 97%; 98%; or 99%) of the unbound and/or bound water that the same ATM would contain at atmospheric pressure when fully hydrated; again measurements of water amounts in the partially hydrated and fully hydrated ATM should be made at the same temperature.

Figure 2:
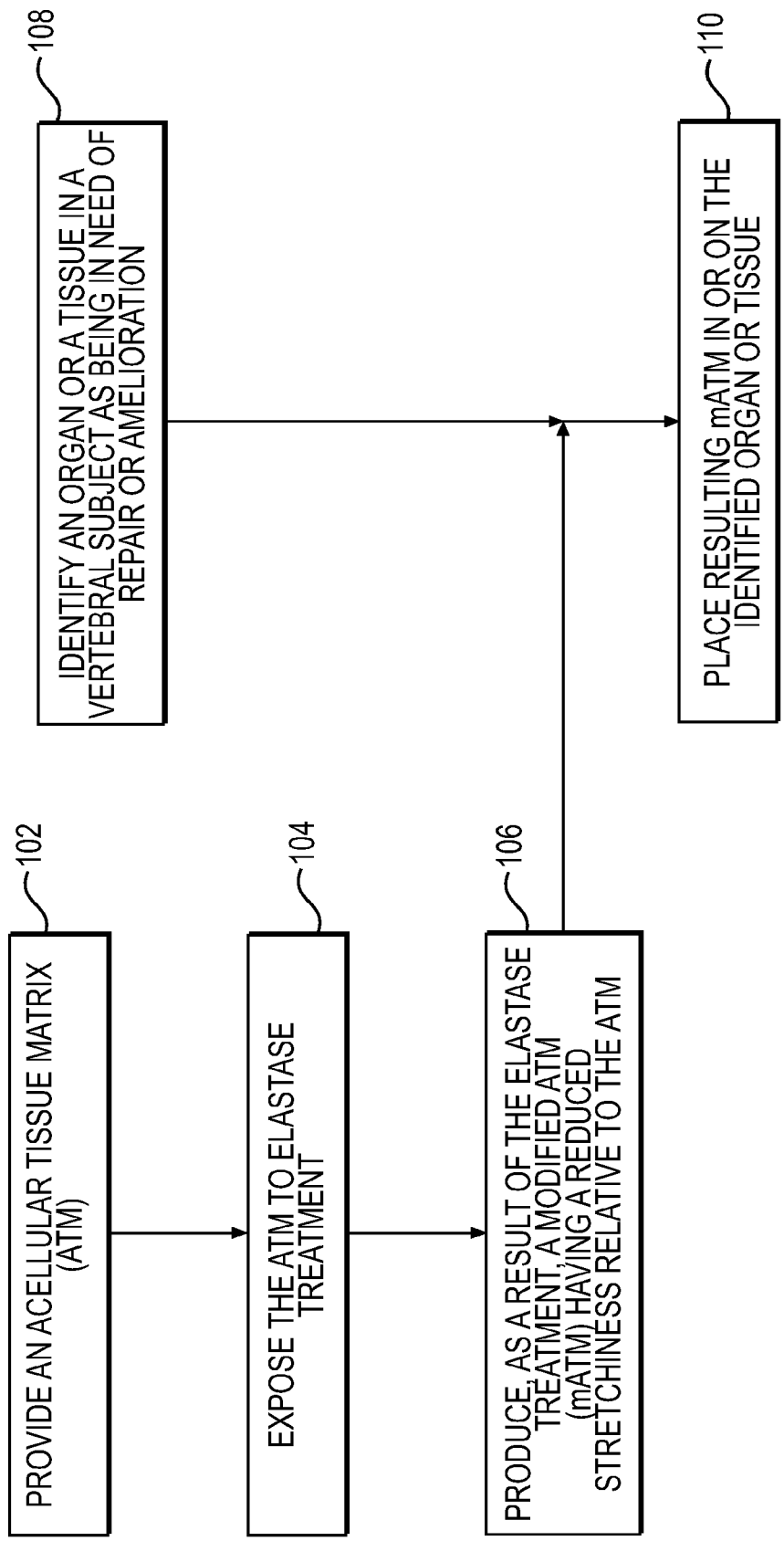
FIG. 2 is a flowchart of a method of treating an acellular tissue matrix (ATM) with elastase and placing the treated ATM in or on an organ or tissue.

FIG. 2 is a flowchart illustrating one implementation of an elastase treatment method. The method includes providing 102 an ATM and exposing 104 the ATM to elastase treatment (discussed below). The elastase treatment produces 106 an mATM having a reduced stretchiness relative to the ATM. If, as shown in the illustrated implementation, an organ or a tissue in a vertebral subject has been identified (e.g., by a medical professional such as a physician) 108 as being in need of repair or amelioration, then the resulting mATM can be placed 110 in or on the identified organ or tissue. It is believed that elastase treatment breaks peptide bonds in the ATM to produce an mATM with a disrupted elastin network. Typically, a sufficient number of peptide bonds are broken to produce some degree of reduced stretchiness in the mATM relative to the ATM. Typically, the number of peptide bonds that are broken is sufficient to the extent that the percent extension (or strain) of mATM under a specific amount of tensile force is less than 95% (e.g., less than: 95%; 90%; 85%; 80%; 75%; 70%; 65%; 60%; 55%; 50%; 45%, 40%, 35%, 30%, 25%, 20%, 15%, 10%, 5% or 2%) of the percent extension (or strain) of ATM under the same amount of tensile force.

As used herein, an "acellular tissue matrix" ("ATM") is a tissue-derived structure that is made from any of a wide range of collagen-containing tissues by removing all, or substantially all, viable cells and all detectable subcellular components and/or debris generated by killing cells. As used herein, an ATM lacking "substantially all viable cells" is an ATM in which the concentration of viable cells is less than 1% (e.g., less than: 0.1%; 0.01%; 0.001%; 0.0001%; 0.00001%; or 0.000001%) of that in the tissue or organ from which the ATM was made. As used herein, a "modified acellular tissue matrix" ("mATM") is an ATM that has been subjected to elastase treatment. Except where otherwise explicitly noted, the various statements herein regarding the use, characteristics, etc. of ATM's apply equally to mATMs.

The ATM of the present disclosure may lack an epithelial basement membrane. The epithelial basement membrane is a thin sheet of extracellular material contiguous with the basilar aspect of epithelial cells. Sheets of aggregated epithelial cells form an epithelium. Thus, for example, the epithelium of skin is called the epidermis, and the skin epithelial basement membrane lies between the epidermis and the dermis. The epithelial basement membrane is a specialized extracellular matrix that provides a barrier function and an attachment surface for epithelial-like cells. Unique components of epithelial basement membranes include, for example, laminin, collagen type VII, and nidogen.

The unique temporal and spatial organization of the epithelial basement membrane distinguish it from, e.g., the dermal extracellular matrix. The presence of the epithelial basement membrane in an ATM of the present disclosure could be disadvantageous in that the epithelial basement membrane may contain a variety of species-specific components that would elicit the production of antibodies, and/or bind to preformed antibodies, in xenogeneic graft recipients of the acellular matrix. In addition, the epithelial basement membrane can act as barrier to diffusion of cells and/or soluble factors (e.g., chemoattractants) and to cell infiltration. Its presence in ATM grafts can thus delay formation of new tissue from the acellular tissue matrix in a recipient animal. As used herein, an ATM that "substantially lacks" an epithelial basement membrane is an acellular tissue matrix containing less than 5% (e.g., less than: 3%; 2%; 1%; 0.5%; 0.25%; 0.1%; 0.01%; 0.001%; or even less than 0.001%) of the epithelial basement membrane possessed by the corresponding unprocessed tissue from which the acellular tissue matrix was derived.

Biological functions retained by ATM include cell recognition and cell binding as well as the ability to support cell spreading, cell proliferation, and cell differentiation. Such functions are provided by undenatured collagenous proteins (e.g., type I collagen) and a variety of non-collagenous molecules (e.g., proteins that serve as ligands for either molecules such as integrin receptors, molecules with high charge density such glycosaminoglycans (e.g., hyaluronan) or proteoglycans, or other adhesins). Structural functions retained by useful acellular matrices include maintenance of histological architecture, maintenance of the three-dimensional array of the tissue's components and physical characteristics such as strength, elasticity, and durability, defined porosity, and retention of macromolecules. The efficiency of the biological functions of an ATM can be measured, for example, by the ability of the ATM to support cell proliferation and is at least 50% (e.g., at least: 50%; 60%; 70%; 80%; 90%; 95%; 98%; 99%; 99.5%; 100%; or more than 100%) of that of the native tissue or organ from which the ATM is made.

While it can be, it is not necessary that the grafted matrix material be made from a tissue or organ that is identical to the surrounding host tissue or organ, but should simply be amenable to being remodeled by invading or infiltrating cells such as differentiated cells of the relevant host tissue, stem cells such as mesenchymal stem cells, or progenitor cells. Remodeling is directed by the above-described ATM components and signals from the surrounding host tissue (such as cytokines, extracellular matrix components, biomechanical stimuli, and bioelectrical stimuli). The presence of mesenchymal stem cells in the bone marrow and the peripheral circulation has been documented in the literature and shown to regenerate a variety of musculoskeletal tissues [Caplan (1991) J. Orthop. Res. 9:641-650; Caplan (1994) Clin. Plast. Surg. 21:429-435; and Caplan Ct al. (1997) Clin Orthop. 342:254-269]. Additionally, the graft should provide some degree (greater than threshold) of tensile and biomechanical strength during the remodeling process.

It is understood that the ATM can be produced from any collagen-containing soft tissue and muscular skeleton (e.g., dermis, fascia, pericardium, dura, umbilical cords, placentae, cardiac valves, ligaments, tendons, vascular tissue (arteries and veins such as saphenous veins), neural connective tissue, urinary bladder tissue, ureter tissue, or intestinal tissue), as long as the above-described properties are retained by the matrix. Moreover, the tissues in or on which the ATM are placed include essentially any tissue that can be remodeled by invading or infiltrating cells. Relevant tissues include, without limitation, skeletal tissues such as bone, cartilage (e.g., articular cartilage), ligaments, fascia, and tendon. Other tissues in which any of the above allografts can be placed include, without limitation, skin, gingiva, dura, myocardium, vascular tissue, neural tissue, striated muscle, smooth muscle, bladder wall, ureter tissue, intestine, and urethra tissue.

Furthermore, while an ATM will generally have been made from one or more individuals of the same species as the recipient of the ATM graft, this is not necessarily the case. Thus, for example, an ATM can have been made from a porcine tissue and be implanted in a human patient. Species that can serve as recipients of ATM and donors of tissues or organs for the production of the ATM include, without limitation, humans, non-human primates (e.g., monkeys, baboons, or chimpanzees), porcine, bovine, horses, goats, sheep, dogs, cats, rabbits, guinea pigs, gerbils, hamsters, rats, or mice. For instance, donors may be animals (e.g., pigs) that have been genetically engineered to lack the terminal galactose-$\alpha$-1, 3 galactose moiety. For descriptions of appropriate animals see co-pending U.S. application Ser. No. 10/896,594 and U.S. Pat. No. 6,166,288, the disclosures of all of which are incorporated herein by reference in their entirety.

The form in which the ATM is provided will depend on the tissue or organ from which it is derived and on the nature of the recipient tissue or organ, as well as the nature of the damage or defect in the recipient tissue or organ. Thus, for example, a matrix derived from a heart valve can be provided as a whole valve, as small sheets or strips, as pieces cut into any of a variety of shapes and/or sizes, or in a particulate form. The same concept applies to ATM produced from any of the above-listed tissues and organs.

The ATM can be produced by a variety of methods. All that is required is that the steps used in their production result in matrices with the above-described biological and structural properties. Useful methods of production include those described in U.S. Pat. Nos. 4,865,871 and 5,366,616 and copending U.S. application Ser. Nos. 09/762,174, 10/165,790, and 10/896,594, all of which are incorporated herein by reference in their entirety.

In brief, the steps involved in the production of an ATM generally include harvesting the tissue from a donor (e.g., a human cadaver or any of the above-listed mammals), chemical treatment so as to stabilize the tissue and avoid biochemical and structural degradation, together with or followed by cell removal under conditions which similarly preserve biological and structural function. After thorough removal of dead and/or lysed cell components that may cause inflammation, as well as any bioincompatible cell-removal agents, the matrix can be subjected to the elastase treatment method of the present disclosure. Alternatively, the ATM can be treated with a cryopreservation agent and cryopreserved and, optionally, freeze dried, again under conditions necessary to maintain the described biological and structural properties of the matrix. After freeze drying, the tissue can, optionally, be pulverized or micronized to produce a particulate ATM under similar function-preserving conditions. After cryopreservation or freeze-drying (and optionally pulverization or micronization), the ATM can be thawed or rehydrated, respectively, and then subjected to the elastase treatment method of the present disclosure. All steps are generally carried out under aseptic, or sterile, conditions.

The initial stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution generally contains an appropriate buffer, one or more antioxidants, one or more oncotic agents, one or more antibiotics, one or more protease inhibitors, and in some cases, a smooth muscle relaxant.

The tissue is then placed in a processing solution to remove viable cells (e.g., epithelial cells, endothelial cells, smooth muscle cells, and fibroblasts) from the structural matrix without damaging the biological and structural integrity of the collagen matrix. The processing solution generally contains an appropriate buffer, salt, an antibiotic, one or more detergents, one or more agents to prevent cross-linking, one or more protease inhibitors, and/or one or more enzymes. Treatment of the tissue should be with a processing solution containing active agents at a concentration and for a time period such that the structural integrity of the matrix is maintained.

After the tissue is decellularized, it can be subjected to the elastase treatment method of the present disclosure or it can be cryopreserved as described below.

Alternatively, the tissue can be cryopreserved prior to undergoing elastase treatment. If so, after decellularization, the tissue is incubated in a cryopreservation solution. This solution generally contains one or more cryoprotectants to minimize ice crystal damage to the structural matrix that could occur during freezing. If the tissue is to be freeze dried, the solution will generally also contain one or more dry-protective components, to minimize structural damage during drying, which may include a combination of an organic solvent and water which undergoes neither expansion or contraction during freezing. The cryoprotective and dry-protective agents can be the same one or more substances. If the tissue is not going to be freeze dried, it can be frozen by placing it (in a sterilized container) in a freezer at about $-80°$ C., or by plunging it into sterile liquid nitrogen, and then storing at a temperature below $-160°$ C. until use. The sample can be thawed prior to use by, for example, immersing a sterile non-permeable vessel (see below) containing a water bath at about 37° C. or by allowing the tissue to come to room temperature under ambient conditions.

If the tissue is to be frozen and freeze dried, following incubation in the cryopreservation solution, the tissue is packaged inside a sterile vessel that is permeable to water vapor, yet impermeable to bacteria, e.g., a water vapor permeable pouch or glass vial. One side of a suitable pouch consists of medical grade porous TYVEK® membrane, a trademarked product of DuPont Company of Wilmington, Del. This membrane is porous to water vapor and impervious to bacteria and dust. The TYVEK® membrane is heat sealed to an impermeable polyethylene laminate sheet, leaving one side open, thus forming a two-sided pouch. The open pouch is sterilized by irradiation (e.g., .gamma.-irradiation) prior to use. The tissue is aseptically placed (through the open side) into the sterile pouch. The open side is then aseptically heat sealed to close the pouch. The packaged tissue is henceforth protected from microbial contamination throughout subsequent processing steps.

The vessel containing the tissue is cooled to a low temperature at a specified rate that is compatible with the specific cryoprotectant formulation to minimize the freezing damage. See U.S. Pat. No. 5,336,616 for examples of appropriate cooling protocols. The tissue is then dried at a low temperature under vacuum conditions, such that water vapor is removed sequentially from each ice crystal phase.

At the completion of the drying of the samples in the water vapor permeable vessel, the vacuum of the freeze drying apparatus is reversed with a dry inert gas such as nitrogen, helium or argon. While being maintained in the same gaseous environment, the semipermeable vessel is placed inside an impervious (i.e., impermeable to water vapor as well as microorganisms) vessel (e.g., a pouch), which is further sealed, e.g., by heat and/or pressure. Where the tissue sample was frozen and dried in a glass vial, the vial is sealed under vacuum with an appropriate inert stopper, and the vacuum of the drying apparatus is reversed with an inert gas prior to unloading. In either case, the final product is hermetically sealed in an inert gaseous atmosphere. The freeze dried tissue may be stored under refrigerated conditions until treated with elastase.

After rehydration of elastase-treated ATM as described below, histocompatible, viable cells can be restored to the ATM to produce a permanently accepted graft that may be remodeled by the host. This is generally done just prior to placing the ATM in a mammalian subject. Where the matrix has been freeze dried, it will be done after rehydration. In one embodiment, histocompatible viable cells may be added to the matrices by standard in vitro cell culturing techniques prior to transplantation, or by in vivo repopulation following transplantation. In vivo repopulation can be by the recipient's own cells migrating into the ATM or by infusing or injecting cells obtained from the recipient or histocompatible cells from another donor into the ATM in situ.

The cell types used for reconstitution will depend on the nature of the tissue or organ to which the ATM is being remodeled. For example, the primary requirement for reconstitution of full-thickness skin with an ATM is the restoration of epidermal cells or keratinocytes. For example, cells derived directly from the intended recipient can be used to reconstitute an ATM, and the resulting composition can be grafted to the recipient in the form of a meshed split-skin graft. Alternatively, cultured (autologous or allogeneic) cells can be added to the ATM. Such cells can be, for example, grown under standard tissue culture conditions and then added to the ATM. In another embodiment, the cells can be grown in and/or on an ATM in tissue culture. Cells grown in and/or on an ATM in tissue culture can have been obtained directly from an appropriate donor (e.g., the intended recipient or an allogeneic donor) or they can have been first grown in tissue culture in the absence of the ATM.

The most important cell for reconstitution of heart valves and vascular conduits is the endothelial cell, which lines the inner surface of the tissue. Endothelial cells may also be expanded in culture and may be derived directly from the intended recipient patient or from umbilical arteries or veins.

Other cells with which the matrices can be repopulated include, but are not limited to, fibroblasts, embryonic stem cells (ESC), adult or embryonic mesenchymal stem cells (MSC), prochondroblasts, chondroblasts, chondrocytes, pro-osteoblasts, osteocytes, osteoclasts, monocytes, pro-cardiomyoblasts, pericytes, cardiomyoblasts, cardiomyocytes, gingival epithelial cells, or periodontal ligament stem cells. Naturally, the ATM can be repopulated with combinations of two more (e.g., two, three, four, five, six, seven, eight, nine, or ten) of these cell types.

Reagents and methods for carrying out all the above steps are known in the art. Suitable reagents and methods are described in, for example, U.S. Pat. No. 5,336,616.

Particulate ATM can be made from any of the above described non-particulate ATM by any process that results in the preservation of the biological and structural functions described above, and damage to collagen fibers, including sheared fiber ends, should be minimized. Many known wetting and drying processes for making particulate ATM do not so preserve the structural integrity of collagen fibers.

One appropriate method for making particulate ATM is described in U.S. Pat. No. 6,933,326. The process is briefly described below with respect to a freeze dried dermal ATM, but one of skill in the art could readily adapt the method for use with freeze dried ATM derived from any of the other tissues listed herein.

The acellular dermal matrix can be cut into strips (using, for example, a Zimmer mesher fitted with a non-interrupting "continuous" cutting wheel). The resulting long strips are then cut into lengths of about 1 cm to about 2 cm. A homogenizer and sterilized homogenizer probe (e.g., a LabTeck Macro homogenizer available from OMNI International, Warrenton, Va.) are assembled and cooled to cryogenic temperatures (i.e., about <196° C. to about −160° C.) using sterile liquid nitrogen that is poured into the homogenizer tower. Once the homogenizer has reached a cryogenic temperature, cut pieces of ATM are added to the homogenizing tower containing the liquid nitrogen. The homogenizer is then activated so as to cryogenically fracture the pieces of ATM. The time and duration of the cryogenic fracturing step will depend upon the homogenizer utilized, the size of the homogenizing chamber, and the speed and time at which the homogenizer is operated. As an alternative, the cryofracturing process can be conducted in a cryomill cooled to a cryogenic temperature.

The cryofractured particulate acellular tissue matrix is, optionally, sorted by particle size by washing the product of the homogenization with sterile liquid nitrogen through a series of metal screens that have also been cooled to a cryogenic temperature. It is generally useful to eliminate large undesired particles with a screen with a relatively large pore size before proceeding to one or more screens with a smaller pore size. Once isolated, the particles can be freeze dried to ensure that any residual moisture that may have been absorbed during the procedure is removed. The final product is a powder (usually white or off-white), generally having a particle size in its longest dimension of about 1 micron to about 900 microns, about 30 microns to about 750 microns, or about 150 to about 300 microns. The material is readily rehydrated by suspension in normal saline or any other suitable rehydrating agent known in the art. It may also be suspended in any suitable carrier known in the art (see, for example, U.S. Pat. No. 5,284,655 incorporated herein by reference in its entirety). If suspended at a high concentration (e.g., at about 600 mg/ml), the particulate ATM can form a "putty", and if suspended at a somewhat lower concentration (e.g., about 330 mg/ml), it can form a "paste". Such putties and pastes can conveniently be packed into, for example, holes, gaps, or spaces of any shape in tissues and organs so as to substantially fill such holes, gaps, or spaces.

One highly suitable freeze dried ATM is produced from human dermis by the LifeCell Corporation (Branchburg, N.J.) and marketed in the form of small sheets as ALLODERM®. Such sheets are marketed by the LifeCell Corporation as rectangular sheets with the dimensions of, for example, 1 cm×2 cm, 3 cm×7 cm, 4 cm×8 cm, 5 cm×10 cm, 4 cm×12 cm, and 6 cm×12 cm. The cryoprotectant used for freezing and drying ALLODERM® is a solution of 35% maltodextrin and 10 mM ethylenediaminetetraacetate (EDTA). Thus, the final dried product contains about 60% by weight ATM and about 40% by weight maltodextrin. The LifeCell Corporation also makes an analogous product made from porcine dermis (designated XenoDerm) having the same proportions of ATM and maltodextrin as ALLODERM®. In addition, the LifeCell Corporation markets a particulate acellular dermal matrix made by cryofracturing ALLODERM® (as described above) under the name CYMETRA®. The particle size for CYMETRA® is in the range of about 60 microns to about 150 microns as determined by mass. In addition, another suitable ATM is a hydrated ATM produced from porcine dermis, STRATTICE™, also available from LifeCell corporation.

The particles of particulate or pulverized (powdered) ATM of the present disclosure will be less than 1.0 mm in their longest dimension. Pieces of ATM with dimensions greater than this are non-particulate acellular matrices.

Elastase Treatment

The term "elastase treatment," as used herein, refers generally to exposing a tissue sample (or samples) to elastase in a manner that disrupts the elastase network of the tissue thereby reducing the stretchiness of the tissue sample(s). Elastase treatment typically is performed anytime after (e.g., immediately after, hours after or days after) a tissue sample has been decellularized. As indicated above, it can also be performed on tissues that have been decellularized and then stored frozen or freeze-dried for long periods of time (e.g., several weeks, months or even years).

Elastase may be obtained from any of a wide variety of sources. It can thus be obtained from animal (e.g., mammalian such as porcine), plant, or microbial (e.g., bacterial) sources. Specific non-limiting examples of elastases that can be used in the methods of the present disclosure are the following:

(a) Porcine pancreatic elastase (Enzyme Commission # EC 3.4.21.36) (pancreatopeptidase E), which is a single polypeptide chain of 240 amino acid residues and contains four disulfide bridges. It has a broad specificity, and will cleave proteins at the carboxyl side of small hydrophobic amino acids such as Ile, Gly, Ala, Ser, Val, and Leu. It will also hydrolyze amides and esters. Porcine pancreatic elastase is unique among proteases in its ability to hydrolyze native elastin, a substrate not attacked by trypsin, chymotrypsin or pepsin. By adding soybean trypsin inhibitor and kallikrein inhibitor, its proteolytic activity, but not its elastolytic activity, is suppressed.

(b) Human neutrophil (leukocyte) elastase (Enzyme Commission # EC 3.4.21.37), which is also known as lysosomal elastase, neutrophil elastase, polymorphonuclear leukocyte elastase, serine elastase, lysosomal elastase, or granulocyte elastase. The 29 KDa serine endoprotease exists as a single 238 amino acid-peptide chain with four disulfide bonds, and shares approximately 43% sequence homology with porcine pancreatic elastase. The leukocyte elastase cleaves preferentially on the carboxyl side of valine, but also cleaves to a lesser extent after (i.e., on the carboxyl side of) alanine. Besides elastin, leukocyte elastase cleaves cartilage proteoglycans, collagen types I, II, II and IV, and fibronectin.

(c) Human matrix metalloproteinase-I2 (MMP-12) (Enzyme Commission # EC 3.4.24.65). MMP-12 is also known as macrophage elastase. It is expressed by a wider range of cells than human leukocyte elastase and is secreted as an inactive enzyme (zymogen). The zymogen is activated by removing the propeptide domain. MMP-12 degrades elastin, collagen IV, laminin, fibronectin, serpins such as alpha-1 proteinase inhibitor, α-2 antiplasmin, and piasminogen activator inhibitor-2, but not interstitial collagens.

(d) Microbial elastases such as *Pseudomonas aeruginosa* elastase, which is a metalloproteinase that hydrolyses insoluble elastin, collagens, immunoglobulins, serum alpha-1-proteinase inhibitor, and alpha-2-macroglobin, laminin and fibrin.

Elastases of interest include: (i) wild-type, full length, mature polypeptides; (ii) functional fragments of (i); (iii) functional variants of (i) and (ii). As used herein, a "fragment" of an elastase polypeptide is a fragment of the corresponding wild-type, full-length, mature elastase that is shorter than the corresponding wild-type, full-length, mature elastase. A variant of an elastase can be a wild-type, full-length, mature elastase, or a fragment of an elastase, that contains one or more internal deletions of 1 to 50, 1 to 25, 1 to 15, 1 to 10, 1 to 8, 1 to 5, or 1 to 3 (e.g., 1, 2, 3, 4, 5, 6, 7, 8, 9, 10, 11, 12, 15, 20, 25, 30, 35, 40, or 50) amino acids, internal or terminal additions of any number of amino acids (e.g., the same numbers given above for internal deletions), or not more than 30 (e.g., not more than: 25; 20; 15; 12; 10; 9; 8; 7; 6; 5; 4; 3; 2; or 1) amino acid substitution(s). Amino acid substitutions may be conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. "Functional" fragments and "functional" variants of an elastase have at least 25% (e.g., at least: 30%; 40%; 50%; 60%; 70%; 80%; 90%; 95%; 97%; 98%; 99%; 99.5%; 100%; or even greater than 100%) of the elastase activity of, the corresponding wild-type, full-length, mature elastase. It is understood from the above that variants can be allelic variants.

In some embodiments, proteolytic inhibitors (e.g., soybean trypsin inhibitor and kallikrein inhibitor) can be included in the elastase-containing media used to treat ATM in order to decrease its broad, non-specific proteolytic activity but retain all or a substantial level (e.g., >40%, >50%, >60%, >70%, >80%, >90%, >95%, >98%, or >99%) of its non-specific proteolytic activity. In addition, functional variants of elastase that, for example, have reduced non-specific proteolytic activity but retained, minimally reduced, or even enhanced elastolytic activity can be useful.

All the elastase wild-type polypeptides, fragments, and variants (referred to collectively below as "elastase polypeptides") described above can be obtained from any relevant natural source by standard biochemical and chemical methods. Alternatively, they can be recombinant molecules produced by standard recombinant methods employing transformed host cells (e.g., eukaryotic, such as mammalian, insect, or fungal, including yeast, cells or prokaryotic cells, such as bacterial cells). Such recombinant methods are well know in the art.

The elastase polypeptides can be used in a crude form (e.g., as a cell lysate or tissue homogenate), in a semi-purified form, or in a substantially pure form. In some embodiments, they may be isolated. The term "isolated elastase polypeptide," as used herein, refers to an elastase polypeptide that either has no naturally-occurring counterpart or has been separated or purified from components that naturally accompany it, e.g., in tissues such as pancreas, liver, spleen, ovary, testis, muscle, joint tissue, neural tissue, gastrointestinal tissue or tumor tissue; body fluids such as blood, serum, or urine; or cells such as leukocytes, monocytic cells, lymphocytic cells, or microbial cells). Typically, an elastase polypeptide is considered "isolated" when it is at least 70%, by dry weight, free from the proteins and other naturally-occurring organic molecules with which it is naturally associated. In various embodiment, a preparation of an elastase polypeptide is at least 80%, at least 90%, or at least 99%, by dry weight, the elastase polypeptide. Since an elastase polypeptide that is chemically synthesized is, by its nature, separated from the components that naturally accompany it, a synthetic elastase polypeptide is "isolated." In addition, an elastase polypeptide, that may be present in culture medium or incubation buffer (used, for example, to treat ATM) due to its presence in mammalian serum (or any other bodily fluid) that the culture medium or incubation buffer contains, is not an isolated elastase polypeptide.

An isolated elastase polypeptide useful for performing the methods of the present disclosure, as indicate above, can be obtained, for example, by extraction from a natural source (e.g., from tissues), by expression of a recombinant nucleic acid encoding the polypeptide; or by chemical synthesis. An elastase polypeptide that is produced in a cellular system different from the source from which it naturally originates is "isolated," because it will necessarily be free of components that naturally accompany it. The degree of isolation or purity can be measured by any appropriate method, e.g., column chromatography, polyacrylamide gel electrophoresis, or HPLC analysis.

In some implementations, elastase treatment is controlled in a manner to obtain a desired degree of stretchiness in the resulting mATM. In those implementations, the desired stretchiness of the resulting mATM may be such that, under an applied tensile force of about 5 newtons/cm, the mATM would extend between about 14% and 24%, between about 15% and 23%, between about 16% and 22%, between about 17% and 21%, between about 18% and 20%, or about 19%. Alternatively, the desired stretchiness may be such that, under an applied tensile force of about 5 newtons/cm, the resulting mATM likely would extend no more than about 24%, 23%, 22%, 21%, 20% or 19%.

Producing an mATM having the desired stretchiness can involve controlling, for example, the duration of exposure and the elastase concentration in the solution to which the tissue sample(s) is exposed. The duration of exposure may be between, for example, about 12 and 24 hours, 13 and 23 hours, 14 and 22 hours, 15 and 21 hours, 16 and 20 hours, 17 and 19 hours or about 18 hours. Alternatively, the duration of exposure may be at least 3 hours, 6 hours, 9 hours or 12 hours. Alternatively, the duration of exposure may be no greater than 30 hours, 18 hours or 9 hours.

The concentration of elastase in solution may be between about 0.1 units/milliliter and 0.5 units/milliliter or between about 0.2 units/milliliter and 0.4 units/milliliter. The concentration of elastase in solution may be about 0.2 units/milliliter, about 0.25 units/milliliter or about 0.3 units/milliliter.

Typically, the amount of elastase solution used to treat a tissue sample(s) is about 3 milliliters per gram of wet tissue. Other amounts of elastase solution may be acceptable as well. For example, more than 3 milliliters per gram of wet tissue certainly should work.

The elastase treatment may be performed at ambient temperatures. As used herein, the term "ambient temperatures" means temperatures between 20-25° C.

Typically, the tissue sample(s) and the elastase solution are agitated during at least part of, if not all of, the duration of elastase exposure.

Methods of Treatment

The form of ATM or mATM used in any particular instance will depend on the tissue or organ to which it is to be applied.

Sheets of ATM (optionally cut to an appropriate size) can be, for example: (a) wrapped around a tissue or organ that is damaged or that contains a defect; (b) placed on the surface of a tissue or organ that is damaged or has a defect; or (c) rolled up and inserted into a cavity, gap, or space in the tissue or organ. Such cavities, gaps, or spaces can be, for example: (i) of traumatic origin, (ii) due to removal of diseased tissue (e.g., infarcted myocardial tissue), or (iii) due to removal of malignant or non-malignant tumors. The ATM can be used to augment or ameliorate underdeveloped tissues or organs or to augment or reconfigure deformed tissues or organs. One or more such strips can be used at any particular site. The grafts can be held in place by, for example, sutures, staples, tacks, or tissue glues or sealants known in the art. Alternatively, if, for example, packed sufficiently tightly into a defect or cavity, they may need no securing device. Particulate ATM can be suspended in a sterile, pharmaceutically acceptable carrier (e.g., normal saline) and injected via hypodermic needle into a site of interest. Alternatively, the dry powdered matrix or a suspension can be sprayed onto into a site of interest. A suspension can also be poured into or onto a particular site. In addition, by mixing the particulate ATM with a relatively small amount of liquid carrier, a "putty" can be made. Such a putty, or even dry particulate ATM, can be layered, packed, or encased in any of the gaps, cavities, or spaces in organs or tissues mentioned above. Moreover, a non-particulate ATM can be used in combination with particulate ATM. For example, a cavity in bone could be packed with a putty (as described above) and covered with a sheet of ATM.

An ATM can be applied to or on a tissue or organ in order to repair or regenerate that tissue or organ and/or a neighboring tissue or organ. Thus, for example, a strip of ATM can be wrapped around a critical gap defect of a long bone to generate a periosteum equivalent surrounding the gap defect and the periosteum equivalent can in turn stimulate the production of bone within the gap in the bone. Similarly, by implanting an ATM in a dental extraction socket, injured gum tissue can be repaired and/or replaced and the "new" gum tissue can assist in the repair and/or regeneration of any bone in the base of the socket that may have been lost as a result, for example, of tooth extraction. In regard to gum tissue (gingiva), receding gums can also be replaced by injection of a suspension, or by packing of a putty of particulate ATM into the appropriate gum tissue. Again, in addition to repairing the gingival tissue, this treatment can result in regeneration of bone lost as a result of periodontal disease and/or tooth extraction. Compositions used to treat any of the above gingival defects can contain one or more other components listed herein, e.g., demineralized bone powder, growth factors, or stem cells.

Both non-particulate and particulate ATM can be used in combination with other scaffold or physical support components. For example, one or more sheets of ATM can be layered with one or more sheets made from a biological material other than ATM, e.g., irradiated cartilage supplied by a tissue bank such as LifeNet, Virginia Beach, Va., or bone wedges and shapes supplied by, for example, the Osteotech Corporation, Edentown, N.J. Alternatively, such non-ATM sheets can be made from synthetic materials, e.g., polyglycolic acid or hydrogels such as that supplied by Biocure, Inc., Atlanta, Ga. Other suitable scaffold or physical support materials are disclosed in U.S. Pat. No. 5,885, 829, the disclosure of which is incorporated herein by reference in its entirety. It is understood that such additional scaffold or physical support components can be in any convenient size or shape, e.g., sheets, cubes, rectangles, discs, spheres, or particles (as described above for particulate ATM).

Active substances that can be mixed with particulate ATM or impregnated into non-particulate ATM include bone powder, demineralized bone powder, and any of those disclosed above.

Factors that can be incorporated into the matrices, administered to the placement site of an ATM graft, or administered systemically include any of a wide range of cell growth factors, angiogenic factors, differentiation factors, cytokines, hormones, and chemokines known in the art. Any combination of two or more of the factors can be administered to a subject by any of the means recited below. Examples of relevant factors include fibroblast growth factors (FGF) (e.g., FGF1-10), epidermal growth factor, keratinocyte growth factor, vascular endothelial cell growth factors (VEGF) (e.g., VEGF A, B, C, D, and E), platelet-derived growth factor (PDGF), interferons (IFN) (e.g., IFN-α, β, or γ), transforming growth factors (TGF) (e.g., TGFα or β), tumor necrosis factor-α, an interleukin (IL) (e.g., IL-I-IL-18), Osterix, Hedgehogs (e.g., sonic or desert), SOX9, bone morphogenic proteins, parathyroid hormone, calcitonin prostaglandins, or ascorbic acid.

Factors that are proteins can also be delivered to a recipient subject by administering to the subject: (a) expression vectors (e.g., plasmids or viral vectors) containing nucleic acid sequences encoding any one or more of the above factors that are proteins; or (b) cells that have been transfected or transduced (stably or transiently) with such expression vectors. In the expression vectors, coding sequences are operably linked to one or more transcription regulatory elements (TRE). Cells used for transfection or transduction can be derived from, or histocompatible with, the recipient. However, it is possible that only short exposure to the factor is required and thus histoincompatible cells can also be used. The cells can be incorporated into the ATM (particulate or non-particulate) prior to the matrices being placed in the subject. Alternatively, they can be injected into an ATM already in place in a subject, into a region close to an ATM already in place in a subject, or systemically.

Naturally, administration of the ATM and/or any of the other substances or factors mentioned above can be single or multiple. Where multiple, the administrations can be at time intervals readily determinable by one skilled in art. Doses of the various substances and factors will vary greatly according to the species, age, weight, size, and sex of the subject, and are also readily determinable by a skilled artisan.

Conditions for which the matrices can be used are multiple. Thus, for example, they can be used for the repair of bones and/or cartilage with any of the above-described damage or defects. Both particulate and non-particulate ATM can be used in any of the forms and by any of the processes listed above. Bones to which such methods of treatment can be applied include, without limitation, long bones (e.g., tibia, femur, humerus, radius, ulna, or fibula), bones of the hand and foot (e.g., calcaneus bone or scaphoid bone), bones of the head and neck (e.g., temporal bone, parietal bone, frontal bone, maxilla, mandible), or vertebrae. As mentioned above, critical gap defects of bone can be treated with ATM. In such critical gap defects, the gaps can be filled with, for example, a putty or packed sheets of ATM and wrapped with sheets of ATM. Alternatively, the gaps can be wrapped with a sheet of ATM and filled with other materials (see below). In all these bone and/or cartilage treatments, additional materials can be used to further assist in the repair process. For example, the gap can be filled with cancellous bone and or calcium sulfate pellets and particulate ATM can be delivered to sites of bone damage or bone defects mixed with demineralized bone powder. In addition, ATM can be combined with bone marrow and/or bone chips from the recipient.

ATM can also be used to repair fascia, e.g., abdominal wall fascia or pelvic floor fascia. In such methods, strips of ATM are generally attached to the abdominal or pelvic floor by, for example, suturing either to the surrounding fascia or host tissue or to stable ligaments or tendons such as Cooper's ligament.

The ATMs are highly suitable for hernia repair. A hernia is the protrusion of the contents of a body cavity out of the body cavity in which the contents are normally found. These contents are often enclosed in the thin membrane that lines the inside of the body cavity; together the membrane and contents are referred to as a "hernial sac." Most commonly hernias develop in the abdomen, when a weakness in the abdominal wall expands into a localized hole or defect through which the intestinal protrusion occurs. These weaknesses in the abdominal wall typically occur in locations of natural thinning of the abdominal wall, that is, at sites where there are natural openings to allow the passage of canals for the blood vessels that extend from the abdomen to the extremities and other organs. Other areas of potential weakness are sites of any previous abdominal surgery. Fatty tissue usually enters a hernia first, but it can be followed by a segment of intestine or other intra-abdominal organ. If a segment of internal organ becomes trapped within the hernia sac such that the blood supply to the organ is impaired, the patient is at risk for serious complications including intestinal blockage, gangrene, and death. Hernias do not heal spontaneously and often increase in size over time, so that surgical repair is necessary to correct the condition. In general, hernias are repaired by reinserting the hernia sac back into the body cavity followed by repair of the weakened muscle tissue.

There are many kinds of hernias. With the exception of inguinal and scrotal hernias, which are only present in males, hernias can be found in individuals of any age or gender. Examples of hernias include: direct inguinal hernias, in which the intestine can bulge into the inguinal canal via the back wall of the inguinal canal; indirect inguinal hernias, in which the intestine can bulge into the inguinal canal via a weakness at the apex of the inguinal canal; fermoral hernias, in which the abdominal contents pass into the weak area created by the passage of the femoral blood vessels into the lower extremities; scrotal hernias, in which the intestinal contents bulge into the scrotum; Spigelian hernia, in which the hernia occurs along the edge of the rectus abdominis muscle; obturator hernia, in which the abdominal contents (e.g., intestine or other abdominal organs) protrude into the obturator canal, lumbar hernias, e.g., Petit's hernia, in which the hernia is through Petit's triangle, the inferior lumbar triangle, and Grynfeltt-Lesshaft's hernia, in which the hernia is through Grynfeltt-Lesshaft triangle, the superior lumbar triangle; Richter's hernia, in which only one sidewall of the bowel becomes strangulated; Hesselbach's hernia, in which the hernia is through Hesselbach's triangle; pantaloon hernia, in which the hernia sac protrudes on either side of the inferior epigastric vessels to give a combined direct and indirect inguinal hernia; Cooper's hernia; epigastric hernia (in which the hernia occurs between the navel and the lower part of the rib cage in the midline of the abdomen); diaphragmatic or hiatal hernias, e.g., Bochdalek's hernia and Morgagni's hernia, in which a portion of the stomach protrudes through the diaphragmatic esophageal hiatus; and umbilical hernia, in which the protrusion is through the navel.

In contrast to hernias of congenital origin, incisional hernias, also known as ventral or recurrent hernias, occur in the abdomen in the area of an old surgical scar. Incisional hernias have a higher risk of returning after surgical repair than do congenital hernias. Moreover, in the case of multiple recurrent hernias, i.e., hernias that recur after two or more repairs have been carried out, the likelihood of successful repair decreases with each subsequent procedure.

Infarcted myocardium is another candidate for remodeling repair by ATM. Contrary to prior dogma, it is now known that not all cardiac myocytes have lost proliferative and thus regenerative potential [e.g., Beltrami et al. (2001) New. Engl. J. Med. 344:1750-1757; Kajstura et al. (1998) Proc. Nat'l. Acad. Sci. USA 95:8801-8805]. Moreover, stem cells, present for example in bone marrow and blood and as pericytes associated with blood vessels, can differentiate to cardiac myocytes. Either the infarcted tissue itself can be removed and replaced with a sheet of ATM cut to an appropriate size or a suspension of particulate ATM can be injected into the infarcted tissue. Congenital heart hypoplasia, or other structural defects, can be repaired by, for example, making an incision in the tissue, expanding the gap created by the incision, and inserting a sheet of ATM cut to the desired size, or placing sheets of ATM on the epicardial and endocardial surfaces and placing particulate ATM between them. It is understood that, in certain conditions, creating a gap by incision may not be sufficient and it may be necessary to excise some tissue. Naturally, one of skill in the art will appreciate that the ATM can be used similarly to repair damage to, or defects in, other types of muscle, e.g., ureter or bladder or skeletal muscle such as biceps, pectoralis, or latissimus.

Moreover, sheets of ATM can be used to repair or replace damaged or removed intestinal tissue, including the esophagus, stomach, and small and large intestines. In this case, the sheets of ATM can be used to repair perforations or holes in the intestine. Alternatively, a sheet of ATM can be formed, for example, into a cylinder which can be used to fill a gap in the intestine (e.g., a gap created by surgery to remove a tumor or a diseased segment of intestine). Such methods can be used to treat, for example, diaphragmatic hernias. It will be understood that an ATM in sheet form can also be used to repair the diaphragm itself in this condition as well as in other conditions of the diaphragm requiring repair or replacement, or addition of tissue.

The following examples serve to illustrate, not limit, the present disclosure.

EXAMPLES

Unless otherwise noted below, ATMs used in the following examples were processed in accordance with LifeCell's proprietary methodology. The methodology for making ATM is broadly described in this example and details for the ATM used in individual experiments are provided in the relevant examples. The description below was that used for the production of ATM from human skin.

Human donor skin was obtained from various U.S. tissue banks and hospitals throughout the nation that collected skin samples from deceased donors after obtaining the consent from family members. Procured skin was placed in RPMI 1640 tissue culture medium containing antibiotics (penicillin and streptomycin) and was shipped to LifeCell's facility in Branchburg, N.J., on wet ice, in the same media. On arrival, the temperature of the skin tissue container is measured, and the skin tissue is discarded if the temperature is above 10° C. The RPMI 1640 medium was changed under aseptic condition and the skin was stored at 4° C., while the serological tests (e.g., RPR, VDRL, HIV I and II, hepatitis B surface antigen, hepatitis C virus and HTLV I and II) were performed. The skin was then transferred to a pre-freezing aqueous solution of 35% w/v maltodextrin. After 2 to 4 hours, the skin was frozen and stored in −80° C. freezer, until it was processed as described below.

Frozen skin was thawed at 37° C. in a water bath until no visible ice was left. The pre-freezing solution was drained before further processing, consisting of the following steps: (i) de-epidermization; (ii) de-cellularization; (iii) wash; (iv) incubation in lyoprotectant solution; (v) freeze-drying.

(i) De-epidermization: Skin epidermis was removed by incubating the tissue sample with gentle agitation in a de-epidermizing solution (1 M NaCl, 0.5% w/v Triton X100, 10 mM EDTA) for 8-32 hours for human skin at room temperature. The epidermal layer was removed from dermis. The epidermis was discarded and the dermis retained for further processing.

(ii) De-cellularization: To remove cellular components, the dermis was rinsed for 5 to 60 minutes with a de-cellularizing solution (2% w/v sodium deoxycholate, 10 mM EDTA, 10 mM HEPES buffer, pH 7.8-8.2), and then incubated with gentle agitation in that solution for 12-30 hours at room temperature.

(iii) Wash: The washing regimen serves to wash out dead cells, cell debris, and residual chemicals using in the previous processing steps. The de-cellularized dermis was transferred to a first wash solution (phosphate buffered saline (PBS) containing 0.5% w/v Triton X-100 and 10 mM EDTA) which was then incubated with gentle agitation for 5 to 60 minutes at room temperature. The dermis was then subjected to three sequential washes in a second wash solution (PBS containing 10 mM EDTA) with gentle agitation at room temperature. The first two washes were short (15-60 minutes each) and the third wash was long (6-30 hours).

(iv) Incubation in cryo-protectant solution. After the wash regiment, the tissue matrix was transferred to a cryo-protectant solution containing 15% w/v maltodextrin for 5-24 hours at room temperature. During the incubation, ATM and solution were agitated.

(v) Freeze-drying. After the cryo-protectant incubation, the resulting ATM was cut into proper sizes, freeze-dried, and then used for the various tests.

Elastase treatment, where implemented, was performed after wash step (iii). The elastase used was natural and extracted from porcine pancreas. The elastase was obtained from the Sigma Aldrich company. Freeze-dried elastase was reconstituted with 200 mM Tris-HCl buffer (pH 8.8) (e.g., stock solution). ATM material from step (ii) was first rinsed with 100 mM Tris-HCl (pH 8.0), and the buffer was drained. After rinsing, 100 mM Tris-HCl (pH 8.0) was added in a volume of about 3 mL per gram of tissue in plastic bottles. Elastase stock solution was added to a final enzyme concentration between about 0.1-0.5 units per mL, and the mixture of tissue material and elastase solution was treated at an ambient temperature (e.g., about 20 to 25° C.) overnight (about 18 to 22 hours).

Effect of Elastase Treatment on Tissue Stretchiness

The effect of elastase treatment on the stretchiness of a tissue sample was studied. Based on that study, we concluded that the stretchiness of a tissue sample likely decreases as a result of exposure to elastase treatment. Moreover, variations in tissue stretchiness can be reduced by exposing a group of tissue samples to elastase treatment.

Example 1

The stretchiness of elastase-treated mATMs was compared to the stretchiness of untreated ATMs. In this example, thirty (30) pairs of tissue samples were obtained. Each pair of tissue samples included one untreated tissue sample and one elastase-treated tissue sample from the same donor lot. All the tissue samples were processed according to LifeCell's proprietary methodology discussed above, with a portion of the tissues being exposed to elastase treatment after the tissue wash (step (iii)). Elastase treatment included placing the tissue samples in a 0.25 units/mL solution of elastase and incubating the mixture of tissue samples and elastase solution for about 20-24 hours at room temperature. After elastase treatment, the tissue samples were washed in a tissue wash solution.

Figure 3:
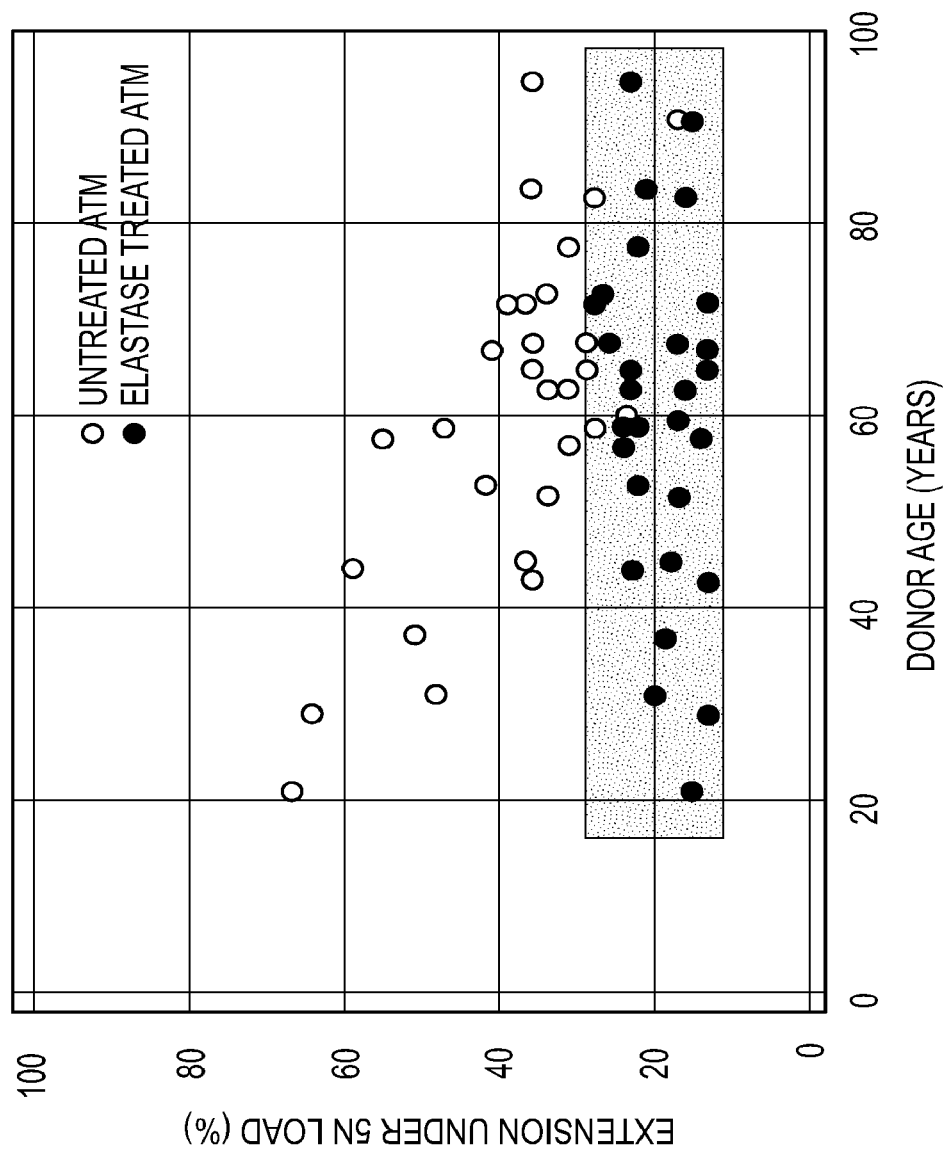
FIG. 3 is a scatter graph showing the percent extension that various about one centimeter long elastase-treated or untreated tissue samples experienced when subjected to an external force of 5 newtons ("5 N").

The elastase-treated tissue samples were compared to a control group of tissue samples that had not been exposed to elastase treatment. In this example, stretchiness is indicated by the percent extension ("%") that an about one centimeter long tissue sample experiences when subjected to a tensile force of approximately 5 Newtons ("5 N"). FIG. 3 is a graph that provides such data for numerous elastase-treated ATMs (darkened circles) and non-elastase-treated ATMs. The graph shows donor ages (in years) on the abscissa (x axis) and shows percent extension under the applied force on the ordinate (y axis). For elastase-treated mATM (darkened circles) data point, there is a corresponding untreated ATM (clear circle) data point from the same donor lot.

The data in the graph shows that the elastase-treated mATMs experienced a smaller percent extension than did their respective corresponding untreated ATMs. As an example, the pair of data points corresponding to the donor age just above twenty, show that the untreated ATM extended more than 60% under the applied tensile force, while the corresponding elastase-treated mATM extended less than 20%. This represents a significant reduction in stretchiness.

Moreover, the data in the graph shows the degree of variation in stretchiness across the population of untreated ATMs (clear circles) is relatively large. Indeed, some of the untreated ATMs extended less than 20%, while others extended more than 60%. In general, untreated ATMs from older donors tended to be less stretchy than untreated ATMs from younger donors.

In marked contrast, the degree of variation in stretchiness across the population of elastase-treated mATMs (darkened circles) is relatively small. Indeed, under the applied tensile force, many of the elastase-treated mATMs extended about 19% and all of the elastase-treated mATMs extended between about 14% and about 24%. This variation in stretchiness (about 14% to about 24%) of the elastase-treated mATMs is indicated by a shaded band in the illustrated graph.

Elastase Concentration as Low as 0.1 Units/Ml was Sufficient

The effectiveness of various elastase concentrations was examined. It was determined that an elastase concentration as low as 0.1 units/milliliter was sufficient to affect the dermal tissue sample's stretchiness.

Example 2

Tissue samples were processed using LifeCell's proprietary methodology, which is described above. After the tissue wash (step iii), the tissue samples were exposed to elastase treatment. During elastase treatment, the tissue samples were exposed to elastase solutions having elastase concentrations of either about 0.1 units/milliliter or about 0.5 units/milliliter, respectively. The elastase solutions were combined with the tissue samples at about 3 milliliters of solution per gram of wet tissue sample. The elastase exposure lasted for about 18 hours. After the elastase exposure, the tissue samples were rinsed with Tris-HC1 buffer, incubated in a freeze drying solution, and freeze dried.

Figure 4A:
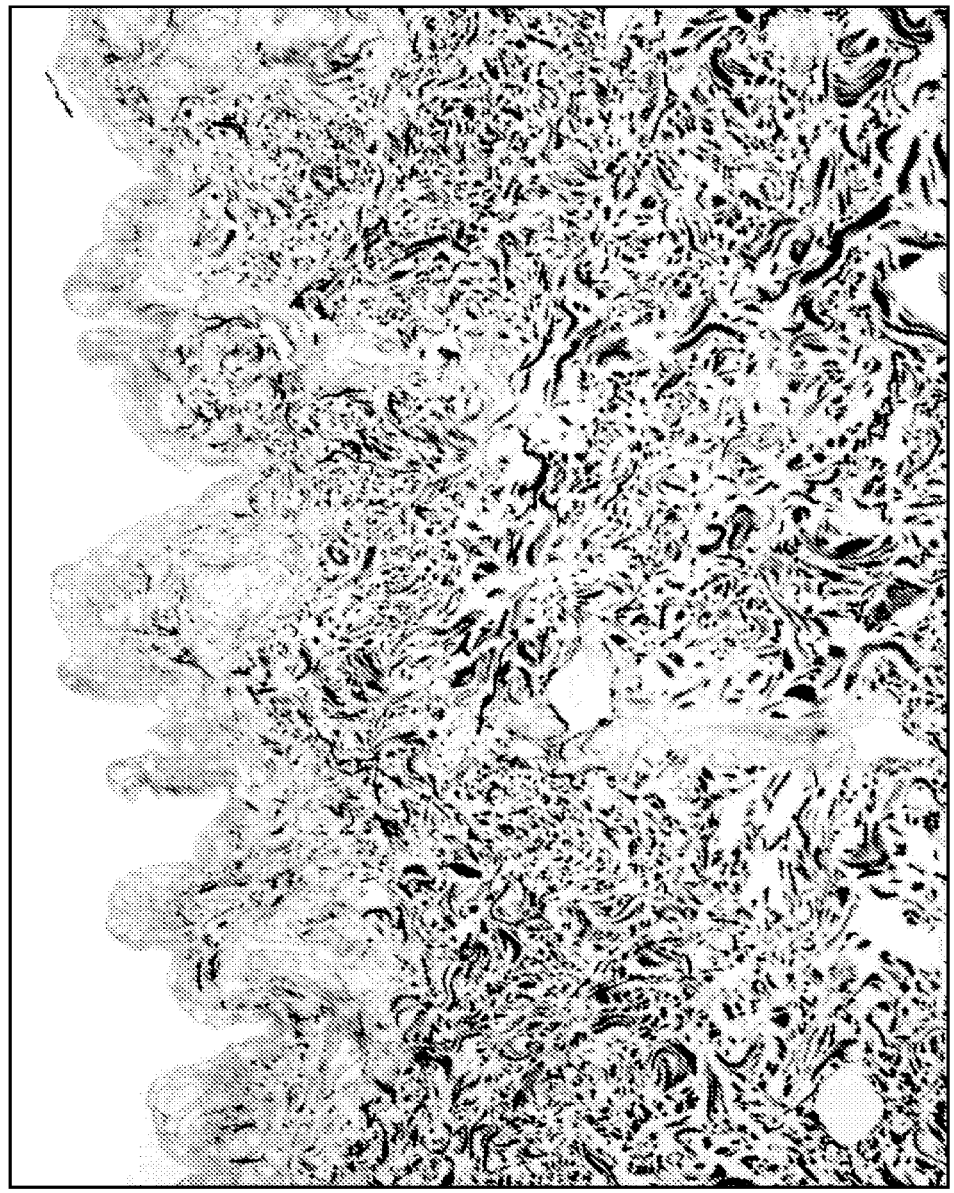
FIGS. 4A and 4B are photomicrographs showing stained samples for an untreated and elastase-treated tissue sample, respectively, where the staining indicates the elastin content of the tissue samples.
Figure 4B:
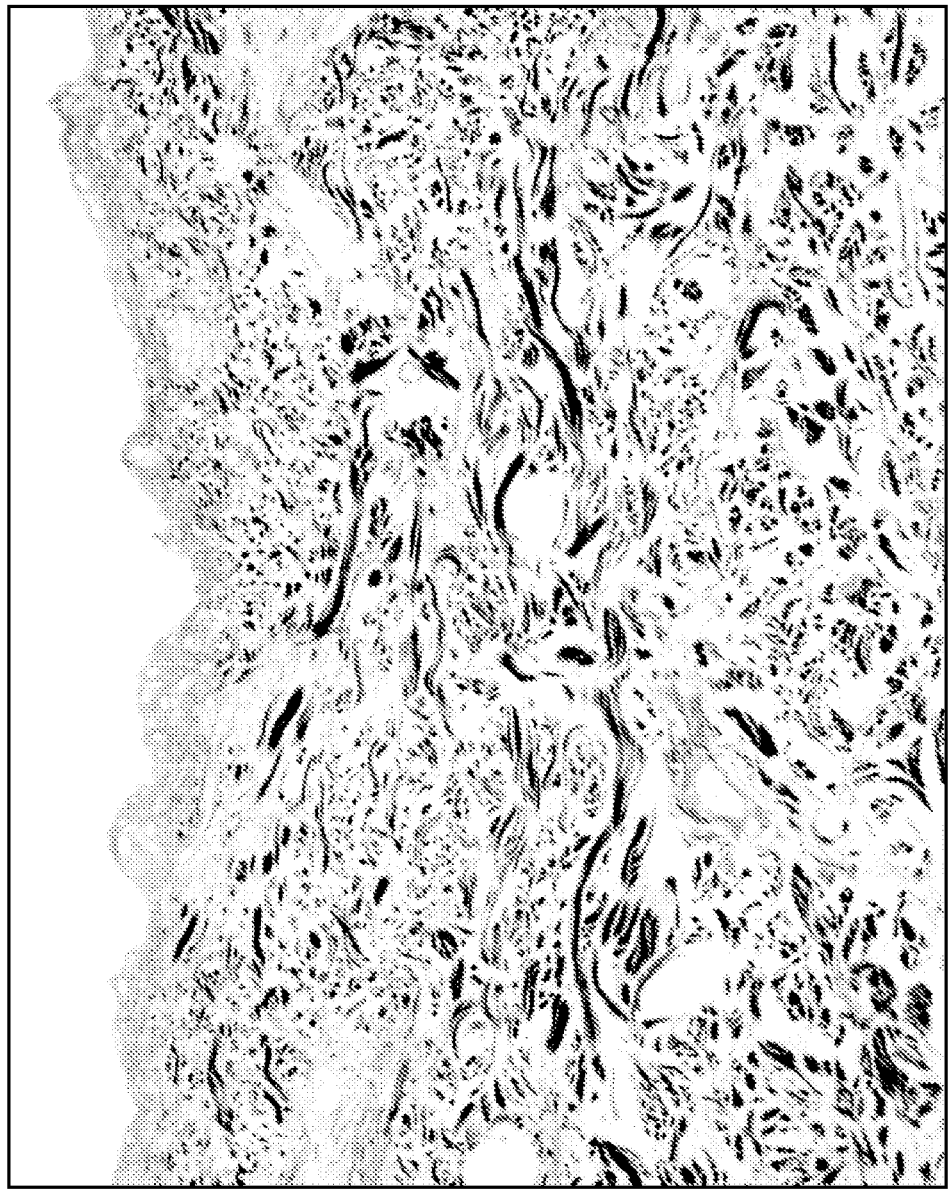

FIGS. 4A and 4B respectively show an untreated tissue sample (FIG. 4A) and a tissue sample that was treated with an elastase solution at a concentration of 0.1 units/milliliter (FIG. 4B). Both samples are Verhoeff's stained. The elastase-treated tissue sample was from the same donor lot as the untreated tissue sample. The shading from the staining shows the tissue samples' respective elastin contents. A visual comparison of FIGS. 4A and 4B reveals that the elastin network in FIG. 4B appears to have been at least partially disrupted. Accordingly, it seems that a solution with an elastase concentration at least as low as 0.1 units/milliliter is sufficient to affect a tissue sample's stretchiness.

It is believed that elastase treatment breaks peptide bonds in the ACM to produce an mATM with a disrupted elastin network. Typically, a sufficient number of peptide bonds are broken to produce some degree of reduced stretchiness in the mATM relative to the ATM. Typically, the number of peptide bonds that are broken is sufficient to the extent that the percent extension (or strain) of mATM under a specific amount of tensile force is less than 95% (e.g., less than: 95%; 90%; 85%; 80%; 75%; 70%; 65%; 60%; 55%; 50%; 45%, 40%, 35%, 30%, 25%, 20%, 15%, 10%, 5% or 2%) of the percent extension (or strain) of the corresponding ATM under the same amount of tensile force.

Tissues Tend to Increase in Size from Elastase Treatment

The effect that elastase treatment has on the size of a tissue sample was studied. Based on that study, it was determined that the size of a tissue samples likely increases as a result of exposure to elastase treatment.

Example 3

The dimensions of thirty-three (33) paired of tissue samples were determined. Each pair of tissue samples included one untreated tissue sample and one elastase-treated tissue sample from the same donor lot. Briefly, the physical dimensions of untreated ATMs from thirty-three (33) donor lots were measured, and the area (i.e., length by width) of each sample was determined. The untreated ATMs were subjected to elastase treatment resulting elastase-treated mATMs. The same physical dimensions of the elastase-treated mATMs were measured, and the area (i.e., length by width) of each elastase-treated mATM was determined. The respective calculated areas for each ATM and mATM pair were compared to determine how much each tissue increased in size as a result of its exposure to elastase treatment.

Figure 5:
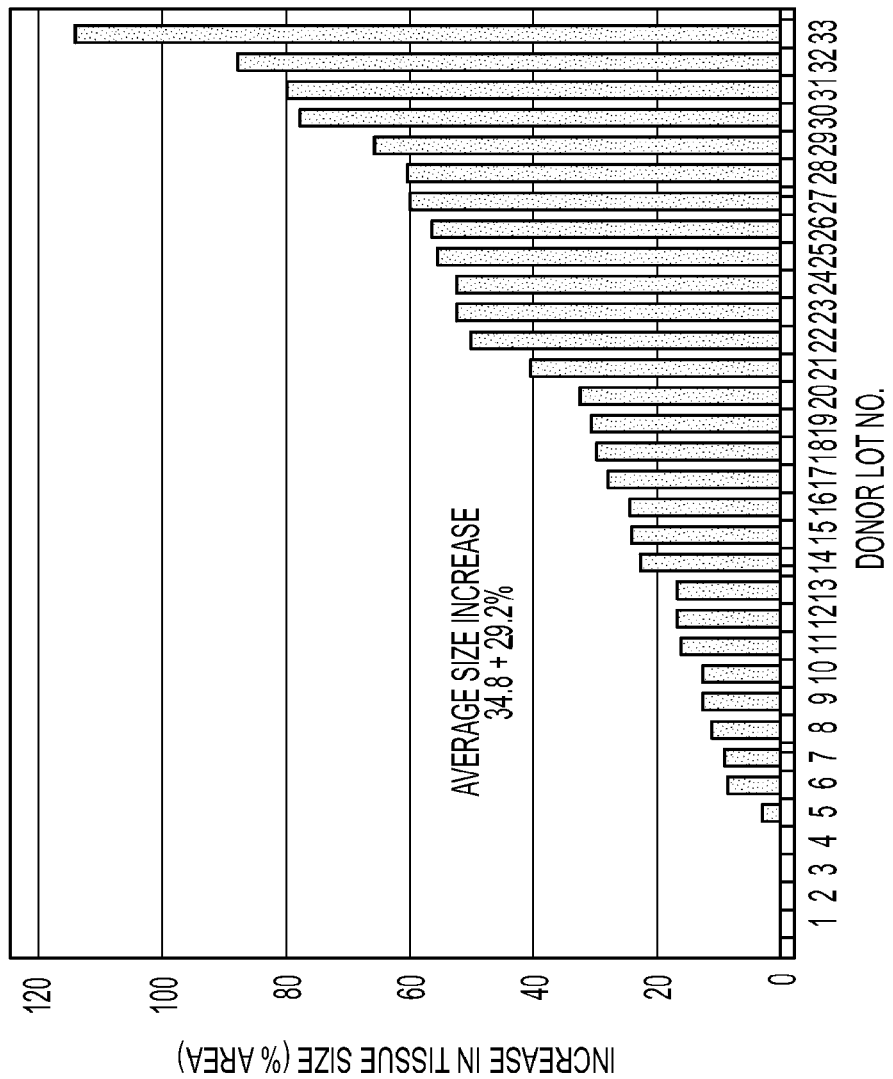
FIG. 5 is a bar graph that shows the percent increase in area that various tissue samples experienced when subjected to elastase treatment.

The graph of FIG. 5 provides the results of this experiment and indicates the percent increase in area that each of the thirty-three tissue samples experienced as a result of the elastase treatment. The graph shows arbitrary donor lot numbers on its abscissa (x axis) and tissue percent increase in area ("% area") on its ordinate (y axis).

The data indicates that some of the tissue samples experienced little to no increase in size. For example, the data that corresponds to donor lot numbers 1-4 show that those tissue samples experienced virtually no increase in size. Other tissue samples, however, experienced a significant increase in size. For example, the data that corresponds to donor lot no. 33 shows that that tissue sample experienced an increase in size of more than 100%.

On average, the tissue samples represented in the graph of FIG. 5 experienced an increase in size of approximately 34.8% with a standard deviation of approximately +/−29.2%.

Example 4

Figure 6:
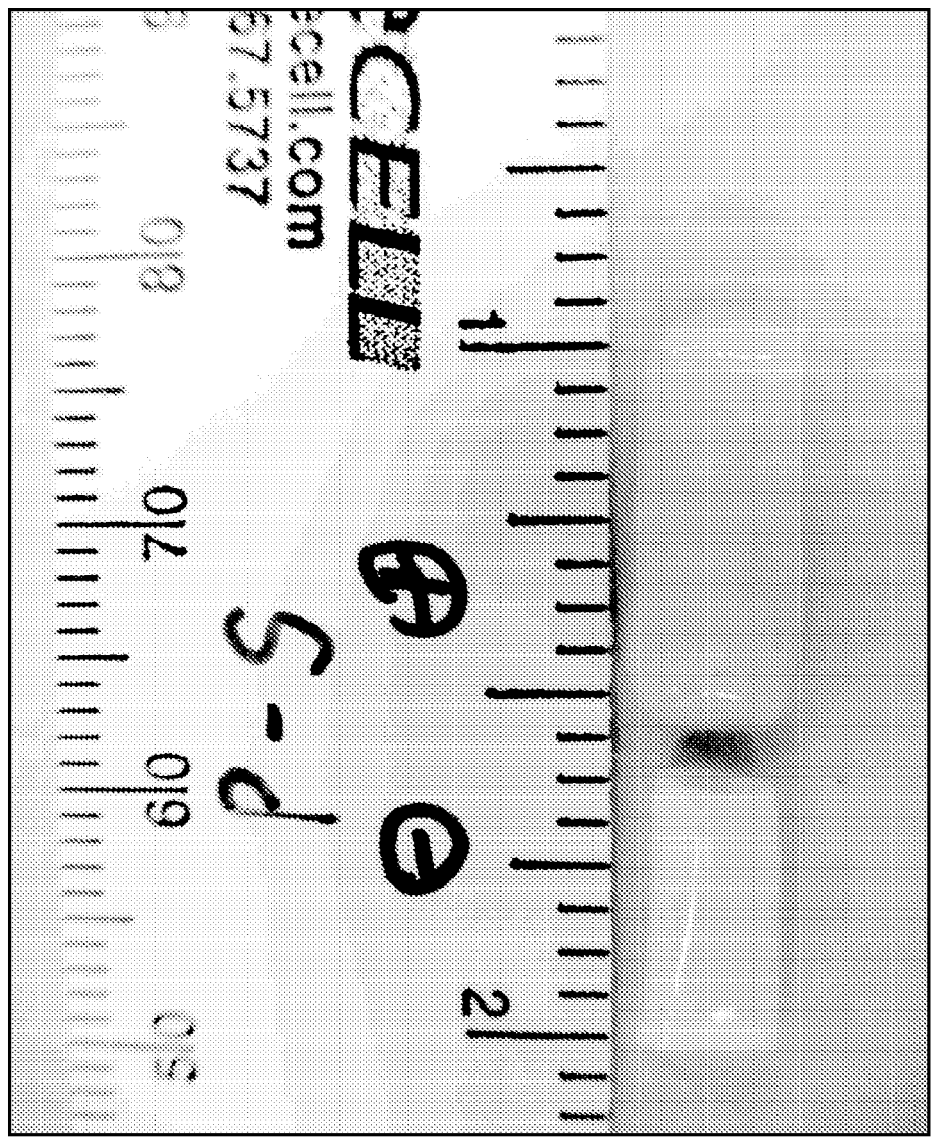
FIG. 6 is a photograph showing an untreated arterial tissue sample and an elastase-treated tissue sample next to a portion of a ruler.

FIG. 6 is a plan view of an untreated ATM 402 next to an elastase-treated mATM 404.

Prior to elastase treatment, tissue samples 402 and 404 were from the same donor lots. They were from the same location of the same animal and had similar physical dimensions (i.e., lengthwise and widthwise) as one another. Visual observation and reference to the ruler reveals that the elastase-treated mATM is clearly larger than the untreated ATM. Indeed, while the untreated ATM 402 has a length of about ⅜ of an inch, the elastase-treated mATM 404 has a length of approximately ⅝ of an inch. Moreover, the elastase-treated mATM 404 clearly is wider than the untreated ATM 402.

Example 5

Table 1 shows physical dimensions of thirty (30) pairs of tissue samples from different donor lots before elastase treatment and after elastase treatment.

TABLE 1

| Lot #. | Before elastase treatment | | After elastase treatment | |
|---|---|---|---|---|
| | Lower D (cm) | Higher D (cm) | Lower D (cm) | Higher D (cm) |
| B20619 | 3.3 | 5.5 | 4.0 | 6.0 |
| B20621 | 3.0 | 6.5 | 3.5 | 8.5 |
| B20623 | 3.5 | 4.0 | 3.5 | 4.5 |
| B20624 | 3.5 | 6.0 | 4.0 | 6.5 |
| B20617 | 3.0 | 4.5 | 3.0 | 4.5 |
| C20646 | 3.0 | 5.0 | 3.5 | 6.0 |
| C20643 | 4.5 | 6.0 | 6.0 | 8.0 |
| C20649 | 6.0 | 8.0 | 6.0 | 9.0 |
| C20651 | 3.0 | 10.0 | 4.0 | 12.0 |
| C20655 | 5.0 | 6.0 | 6.0 | 7.5 |
| B20664 | 2.0 | 8.0 | 3.0 | 10.0 |
| B20669 | 2.5 | 5.0 | 2.5 | 6.5 |
| B20672 | 3.5 | 6.0 | 4.0 | 8.0 |
| B20673 | 2.5 | 6.0 | 2.5 | 7.0 |
| B20673 | 3.5 | 4.5 | 3.5 | 5.0 |
| B20747 | 3.5 | 3.5 | 4.5 | 4.5 |
| B20749 | 4.2 | 6.0 | 6.0 | 9.0 |
| B20752 | 4.0 | 6.0 | 5.0 | 7.5 |
| B20753 | 3.0 | 8.0 | 3.5 | 11.0 |
| B20759 | 3.0 | 7.5 | 3.5 | 7.0 |
| B20837 | 5.0 | 6.0 | 5.0 | 7.0 |
| B20842 | 5.5 | 8.5 | 6.8 | 10.8 |
| B20844 | 5.0 | 8.0 | 6.0 | 8.3 |
| B20849 | 7.5 | 10.0 | 7.0 | 11.0 |
| B20855 | 5.0 | 6.0 | 5.0 | 6.5 |
| B20908 | 3.0 | 4.0 | 3.0 | 4.5 |
| B20900 | 4.0 | 6.0 | 4.0 | 6.0 |
| B20911 | 4.0 | 5.0 | 4.0 | 5.0 |
| B20914 | 3.0 | 5.7 | 3.5 | 6.3 |
| B20915 | 2.3 | 3.3 | 3.0 | 3.3 |

The physical dimensions include, for tissue samples before and after elastase treatment, a smaller dimension in centimeters ("cm"), identified as "Lower D (cm)" and a larger dimension in centimeters ("cm"), identified as "Higher D (cm)."

The data shows that elastase treatment caused increases in the smaller or larger dimension that ranged from 0% to 50%. For most of the tissue samples, the data shows that at least one of the measured dimensions increased in size from the elastase treatment. The mean increase in size in the smaller dimension was 14.7% with a standard deviation of 14.5%. The mean increase in size in the larger dimension was 17.3% with a standard deviation of 13.0%.

Effect of Elastase Treatment on Elastin Content

The effect of elastase treatment on elastin content in a tissue was considered. Elastin content analysis was performed using a FASTIN™ Elastin Assay, available from Bicolor Ltd, UK, which involves specific dye binding using a synthetic porphyrin (5, 10, 15, 20 tetraphenyl-21, 25 porphyrin in a sulfonate form).

Example 6

Table 2 shows elastin content in tissue samples from thirty (30) different paired donor lots before elastase treatment and after elastase treatment. The elastin content was measured using the FASTIN™ Elastin Assay. Before elastase treatment, the elastin content ranged from about 1.6% to about 5.1% by weight. After elastase treatment, the elastin content ranged from about 1.4% to about 6.1%.

TABLE 2

| Lot # | Before elastase treatment | After elastase treatment |
|---|---|---|
| B20619 | 2.3% | 2.2% |
| B20621 | 2.3% | 2.4% |
| B20623 | 2.8% | 2.3% |
| B20624 | 2.8% | 2.1% |
| B20617 | 1.9% | 2.1% |
| C20646 | — | 1.8% |
| C20643 | 2.6% | 2.4% |
| C20649 | 3.1% | 2.5% |
| C20651 | 1.9% | 1.8% |
| C20655 | 1.6% | 2.0% |
| B20664 | 2.5% | 3.2% |
| B20669 | 2.9% | 2.0% |
| B20672 | 1.9% | 1.4% |
| B20673 | 2.3% | 1.8% |
| B20679 | 2.3% | 1.7% |
| B20747 | 3.7% | 1.8% |
| B20749 | — | 2.6% |
| B20752 | 2.2% | 1.9% |
| B20753 | 2.7% | 1.9% |

TABLE 2-continued

| Lot # | Before elastase treatment | After elastase treatment |
|---|---|---|
| B20759 | 2.6% | 2.0% |
| B20837 | 2.4% | 2.4% |
| B20842 | 2.2% | 2.2% |
| B20844 | 2.7% | 1.9% |
| B20849 | 3.8% | 3.1% |
| B20855 | 2.3% | 1.4% |
| B20908 | 2.9% | 3.8% |
| B20900 | 3.7% | 6.1% |
| B20911 | 5.1% | 3.9% |
| B20914 | 4.0% | 2.1% |
| B20915 | 3.2% | 2.5% |

The data shown in Table 2 indicates that elastase treatment caused the elastin content to increase in some of the donor lots and decrease in others. However, the apparent increases are within the error/uncertainty of measurements. When one looks at the average of all materials, the elastin content decreases a little bit.

According to the data, before elastase treatment, the mean value of elastin content in the group of tissue samples was 2.74%, with a standard deviation of +/−0.76%. After elastase treatment, the mean value of elastin content in the group of tissue samples was 2.38%, with a standard deviation of +/−0.92%.

The elastase treatment, therefore, produced a statistically significant, but small loss in elastin content. It is believed that after elastase treatment, elastin in the form of fragmented elastin was present in the tissue samples.

Effect on Tissue Sample's Tensile Properties

The effect of elastase treatment on a various tensile properties of a tissue sample was considered.

Example 7

In this example, tests were conducted on tissue samples from thirty (30) paired donor lots. Each pair of tissue samples included one untreated tissue sample and one elastase-treated tissue sample from the same donor lot. In other words, for each donor lot, there are elastase-treated tissue samples and non-treated samples. Each tissue sample was subjected to testing to determine its maximum load, tensile stress, percent strain and Young's modulus. The results of those tests are summarized in Table 3.

TABLE 3

| Treatment | Maximum Load (N/cm) | Tensile stress at Maximum load (MPa) | Strain at 5 N/cm (%) | Young's modulus (MPa) |
|---|---|---|---|---|
| Regular ALLODERM® | 170 ± 109 | 7.5 ± 3.9 | 39 ± 14 | 24.7 ± 11.7 |
| Elastase-treated RTM | 176 ± 110 | 7.9 ± 4.4 | 19 ± 5 | 31.3 ± 17.3 |
| P-value | 0.330 | 0.220 | 0.000 | 0.004 |

Referring to Table 3, the maximum load reflects the maximum force per centimeter in newtons per centimeter ("N/cm") that the tissue samples were able to withstand before breaking. As shown in the table, the mean maximum load that the non-elastase-treated tissue samples (identified as "regular ALLODERM®" in the table) could withstand was 170 newtons/centimeter, with a standard deviation of 109 newtons/centimeter. The mean maximum load that the elastase-treated tissue samples (identified as "Elastase-treated RTM" in the table) could withstand was 176 newtons/centimeter, with a standard deviation of 110 newtons/centimeter. The p-value for the collected maximum load data, which generally represents the probability that the observed results (or results more extreme) could have occurred by chance, was 0.330. The likelihood that elastase treatment might adversely affect a tissue sample's maximum load capacity seems small.

Tensile stress provides a measure of the internal distribution of force per unit area that balances and reacts to an external applied load. Tensile stress at the maximum load (or known as the tensile strength) is the maximum tensile stress the tissue can withstand before breaking. The mean tensile stress at the maximum load in megapascals (MPa) of the non-elastase-treated tissue samples was 7.5, with a standard deviation of 3.9. The mean tensile stress at the maximum load of the elastase-treated tissue samples was 7.9, with a standard deviation of 4.4. The p-value for the collected tensile stress data was 0.220. The likelihood that elastase treatment might significantly alter a tissue sample's tensile strength seems small.

The strain values provide a measure of the deformation that occurs in a tissue sample as the result of an externally applied load. The mean percent strain (percent extension) of non-elastase-treated tissue samples under a 5 newtons/centimeter force was 39%, with a standard deviation of 14%. The mean percent strain (percent extension) of the elastase-treated tissue samples under the same load was 19%, with a standard deviation of 5%. The p-value for the collected strain data was 0.000. In view of the foregoing, the treatment reduces tissue stretchiness, and increase the consistence in tissue elasticity and stiffness.

Young's modulus reflects the resistance of the tissue samples to elongation when an external force is applied. The mean Young's modulus, in megapascals ("MPa"), for the non-elastase-treated tissue samples was 24.7 megapascals, with a standard deviation of 11.7 megapascals. The mean Young's modulus for the elastase-treated tissue samples was 31.3 megapascals, with a standard deviation of 17.3 megapascals. The p-value for the collected Young's modulus data was 0.004. In view of the foregoing, the treatment increases stiffness.

The maximum load, tensile strength and Young's modulus data in Table 3 indicates that the effect of elastase treatment on those properties is negligible.

Example 8

Tissue samples from two donor lots were processed in accordance with LifeCell's proprietary methodology discussed above. After the tissue wash (step (iii)), the tissue samples were cut into multiple 1 centimeter×7 centimeter pieces. Some of those pieces were exposed to elastase treatment.

Untreated and elastase-treated tissue samples from the two donor lots were subjected to testing to determine their thickness, maximum load, tensile stress, elasticity, percent strain and Young's modulus. Each of these parameters was discussed in some detail above, except thickness and elasticity. Thickness is a physical dimension of the tissue and, in the illustrated table, is measured in millimeters ("mm"). Elasticity refers generally to the tendency of a body to return to its original shape after it has been stretched or compressed and, in the illustrated table, is measured in newtons/centimeter ("N/cm")

The results of the foregoing tests are summarized in Table 4. The data in that table indicates that, with the possible exception of strain at 5 newtons/centimeter, elastase treatment did not significantly alter any of the tested properties. For the tissue samples in donor lot #40765, for example, elastase treatment resulted in a change in mean strain (at 5 newtons/centimeter) from 0.3 5% to 0.2% (significantly decreased). For tissue samples in donor lot #24750, elastase treatment resulted in a change in mean strain from 0.19% to 0.22% (no significant difference).

TABLE 4

| Treatment | Thickness (mm) | Maximum load (N/cm) | Tensile stress at maximum load (MPa) | Elasticity (N/cm) | Strain at 5 N/cm (%) | Young's modulus (MPa) |
|---|---|---|---|---|---|---|
| Lot # 40765 (N = 11) | | | | | | |
| Control | 3.87 ± 0.87 | 197 ± 47 | 5.4 ± 1.8 | 439 ± 121 | 0.35 ± 0.10 | 12.0 ± 4.3 |
| Elastase | 3.93 ± 0.92 | 173 ± 37 | 4.6 ± 1.5 | 503 ± 86 | 0.20 ± 0.03 | 13.4 ± 3.4 |
| Lot # 24750 (N = 12) | | | | | | |
| Control | 1.66 ± 0.21 | 146.4 ± 45 | 8.8 ± 2.2 | 541 ± 195 | 0.19 ± 0.03 | 33.1 ± 12.0 |
| Elastase | 1.86 ± 0.22 | 145.5 ± 30 | 7.9 ± 1.6 | 498 ± 145 | 0.22 ± 0.03 | 27.2 ± 8.9 |

Effect on Tissue Sample's Histology

The effect of elastase treatment on a tissue sample's histology also was considered.

More particularly, various histological parameters were considered for twelve (12) pairs of freeze-dried tissue samples. Each pair of tissue samples included one untreated tissue sample and one elastase-treated tissue sample from the same donor lot.

Example 10

Table 5 shows the results of the tissue sample histology testing. Each row in the column corresponds to one tissue sample that was tested. The first column of the table identifies the corresponding tissue sample's donor lot number, an arbitrary designation. The second column of the table indicates whether the corresponding tissue sample had been exposed to elastase treatment. The designation "no elastase" means that the corresponding tissue sample was untreated, while the designation "elastase" indicates that the corresponding tissue sample had been exposed to elastase treatment. The data in the first twelve rows and the data in the second twelve rows correspond to tissue samples from the same groups of donor lots.

The third, fourth, fifth and sixth columns of the table indicate the total holes, collagen damage, papillary to reticular transition and collagen separation in the corresponding tissue samples.

Holes in the tissue samples may represent a variety of structures including blood vessels, empty adipocytes, vacant hair follicles, and expansion of gas bubbles within the sample during the freeze-drying process. Histologically, it is difficult to distinguish between these, and hence the presence of holes is graded according to the total percentage area of the sample occupied by these structures. Scoring:

| Score | Assessment |
|---|---|
| 1-2 | Holes in 0%-10% of the sample. |
| 3-4 | Holes in 11%-25% of the sample. |
| 5-6 | Holes in 26%-40% of the sample. |
| 7-9 | Holes in 41%-60% of the sample. |
| 10 | Holes in >60% of the sample. |

"Collagen damage" refers to the presence of broken collagen fibers, condensed collagen fibers, or distorted fibers. Collagen damage is reported as incidence of observation in visual fields for all samples. Scoring:

| Score | Assessment |
|---|---|
| 1-2 | Damage in 0%-10% of the fields examined. |
| 3-4 | Damage in 11%-25% of the fields examined. |
| 5-6 | Damage in 26%-50% of the fields examined. |
| 7-8 | Damage in 51%-75% of the fields examined. |
| 9-10 | Damage in 76%-100% of the fields examined. |

Regarding papillary-to-reticular transition, normal human dermis contains a papillary layer consisting of a superficial basement membrane zone and then a layer of vascular and amorphous structure lacking clearly defined thick bundles of collagen. The collagen and elastin appearance of the papillary layer is one of fine reticulation. The reticular layer merges with the papillary layer and is composed of clearly defined collagen bundles. If collapse or melting occurs during processing of the tissue to produce the ATM, there will be a condensation of the papillary layer. If skin is extensively scarred or subject to a pathological process such as scleroderma or epidermolysis, there will be a loss of the papillary layer. If samples lack a papillary layer, the relevant lot was rejected. Scoring:

| Score | Assessment |
|---|---|
| 0 | Normal bilayer, clearly defined vascular plexus, clear transition. |
| 0-2 | poorly defined undulations of rete ridge and rete peg. |
| 0-2 | Loss of structural features in superficial papillary layer, including vascular plexus. |
| 0-2 | Loss of structural features in inner papillary layer. |
| 0-2 | Loss of transition zone between papillary and reticular layer. |
| 10 | Absence or replacement of papillary layer with amorphous condensed layer. |

Collagen Separation: Normal collagen in an ATM should have an internal fibrous structure, and separation between bundles should represent a gradual transition from one fiber to the next. Collagen separation is a recognized change that occurs in processing. At its extreme, the collagen fiber loses its fibrous nature and appears amorphous, the separation between fibers becomes an abrupt transition, and the fibers often appear angulated. Based on animal and clinical evaluation, no functional significance can to date be attributed to this appearance. However, although not grounds for rejection alone, this is included as part of the assessment of matrix integrity.

| Score | Assessment |
|---|---|
| 1 | No artificial separation, fibrous structure evident. |
| 3 | Sharp separation, some fibrous definition. |
| 5 | Angular separation, amorphous collagen appearance. |

The foregoing parameters were determined based on hematoxylin & eosin (H & E) staining. The data in the table does not show a significant difference in the indicated histological parameters for elastase-treated tissue samples as compared to non-elastase-treated tissue samples.

TABLE 5

| Lot # | Treatment | Total holes | Collagen damage | Papillary to reticular transition | Collagen separation |
|---|---|---|---|---|---|
| B20747 | No elastase | 9 | 9 | 8 | 4 |
| B20749 | No elastase | 8 | 9 | 7 | 4 |
| B20752 | No elastase | 7 | 8 | 7 | 4 |
| B20753 | No elastase | 8 | 10 | 7 | 4 |
| B20759 | No elastase | 8 | 9 | 8 | 4 |
| B20837 | No elastase | 8 | 10 | 8 | 4 |
| B20842 | No elastase | 6 | 9 | 8 | 4 |
| B20844 | No elastase | 5 | 10 | 10 | 4 |
| B20849 | No elastase | 9 | 10 | 10 | 5 |
| B20855 | No elastase | 5 | 8 | 7 | 3 |
| 40765 | No elastase | 6 | 8 | 7 | 4 |
| 24750 | No elastase | 7 | 8 | 8 | 4 |
| B20747 | Elastase | 6 | 8 | 10 | 4 |
| B20749 | Elastase | 7 | 9 | 8 | 4 |
| B20752 | Elastase | 5 | 7 | 8 | 3 |
| B20753 | Elastase | 6 | 8 | 7 | 4 |
| B20759 | Elastase | 7 | 9 | 8 | 4 |
| B20837 | Elastase | 7 | 10 | 10 | 5 |
| B20842 | Elastase | 6 | 8 | 8 | 4 |
| B20844 | Elastase | 5 | 9 | 8 | 4 |
| B20849 | Elastase | 8 | 10 | 8 | 5 |
| B20855 | Elastase | 5 | 9 | 8 | 4 |
| 40765 | Elastase | 8 | 8 | 8 | 3 |
| 24750 | Elastase | 9 | 9 | 8 | 3 |

Example 11

Figure 7:
FIG. 7 is a series of photographs showing a series of Verhoeffs' stained samples for untreated (regular ALLODERM®) and elastase-treated tissue samples.
Figure 7:
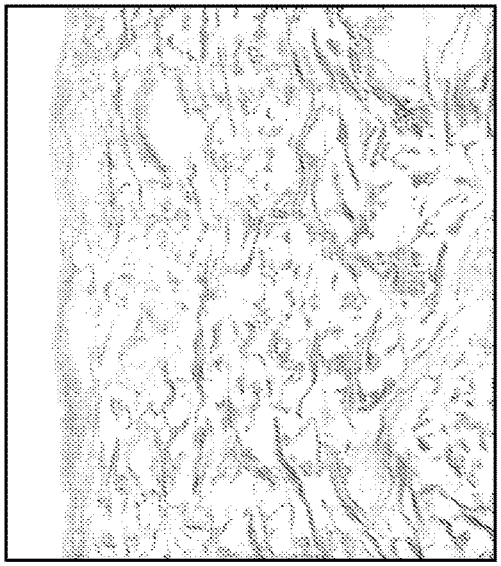
Figure 7:
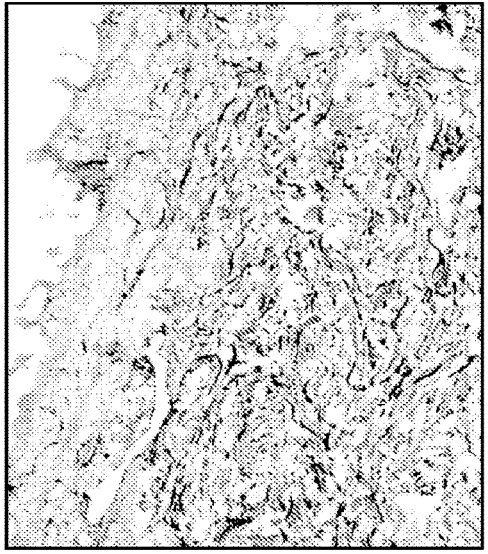
Figure 7:
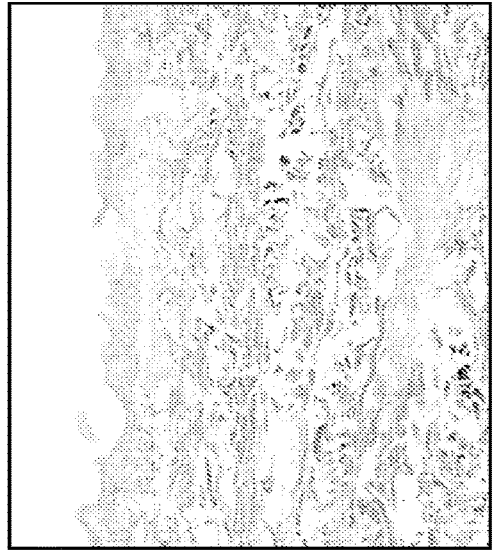

FIG. 7 shows exemplary Verhoeff's stains for paired tissue samples from two of the donor lots in Example 10 (and indicated in Table 5). As indicated above, each pair of tissue samples includes one untreated tissue sample (identified as "Regular ALLODERM®" in FIG. 7) and one elastase-treated tissue sample (identified as "Elastase-Treated" in FIG. 7). Darkened portions of the stain show the elastin structure of the tissues. For each pair of tissue samples, the Verhoeff stains suggest that elastase treatment does not cause substantial fragmentation or disruption of the tissue samples' complex elastin structure.

Example 12

Figure 8:
FIG. 8 is a series of photomicrographs showing Alcian blue stained tissue samples for untreated (regular ALLODERM®) and elastase-treated tissue samples.
Figure 8:
Figure 8:
Figure 8:

FIG. 8 shows examples of Alcian blue stains for paired tissue samples from two of the donor lots in Example 10 (and indicated in Table 5). Each pair of tissue samples includes one untreated tissue sample (identified as "Regular ALLODERM®" in FIG. 8) and one elastase-treated tissue sample (identified as "Elastase-Treated" in FIG. 8).

For each pair of tissue samples, the Alcian blue stains show a slight reduction in stain intensity in the elastase-treated tissue samples as compared to their corresponding non-elastase-treated tissue samples. This reduction in stain intensity suggests partial loss in glycosaminoglycan (GAG), presumably due to an extended time in the aqueous processing solution.

Effect of Elastase Treatment on Tissue Sample's Thermal Stability

Example 13

Differential scanning calorimetry (DSC) analysis was used to investigate changes in thermal stability of tissue samples after elastase treatment in twelve (12) paired donor lots. Table 6 shows onset denaturation temperature measured in degrees Celsius ("Onset Tm (° C.)") and denaturation enthalpy represented in Joules per gram dry weight ("J/gdw") for tissue samples from various donor lots. Denaturation refers to a change in a tissue structure by the application of heat, for example. The onset denaturation temperature is the temperature at which denaturation begins to occur. Denaturation enthalpy is a measure of energy needed to denature the tissue collagen and other proteins.

Each row in the column corresponds to a particular tissue sample that was tested. The first column of the table identifies the corresponding tissue sample's donor lot number. The second column of the table indicates whether the corresponding tissue sample was exposed to elastase treatment. The designation "no elastase" indicates that the corresponding tissue sample was not exposed to elastase treatment. The designation "elastase" indicates that the corresponding tissue sample was exposed to elastase treatment. The first twelve rows of data correspond to tissue samples that were not exposed to elastase treatment. The last twelve rows of data correspond to tissue samples that were exposed to elastase treatment. The data in the first twelve rows and the data in the second twelve rows correspond to tissue samples from the same groups of donor lots.

The third and fourth columns of the table show the onset denaturation temperature and the denaturation enthalpy for each corresponding tissue sample.

The data in the table shows no significant difference in onset denaturation temperature or denaturation enthalpy for elastase-treated tissue samples as compared to non-elastase-treated tissue samples. The mean onset denaturation temperature for non-elastase-treated tissue samples was 60.9° C. with a standard deviation of approximately +/−1.3° C. The mean onset denaturation temperature for the elastase-treated tissue samples was 60.8° C., with a standard deviation of approximately +/−1.2° C. The mean denaturation enthalpy for the non-elastase-treated tissue samples was 25.8 J/gdw, with a standard deviation of +/−2.7 J/gdw. The mean denaturation enthalpy for the elastase-treated tissue samples was 28.1, with a standard deviation of +/−3.5.

TABLE 6

| Lot #. | Treatment | Onset Tm (° C.) | Enthalpy (J/gdw) |
|---|---|---|---|
| B20747 | No elastase | 60.45 | 26.21 |
| B20749 | No elastase | 63.27 | 29.02 |
| B20752 | No elastase | 61.32 | 22.40 |
| B20753 | No elastase | 60.48 | 22.10 |
| B20759 | No elastase | 59.78 | 28.57 |
| B20837 | No elastase | 60.66 | 28.79 |
| B20842 | No elastase | 60.25 | 25.06 |
| B20844 | No elastase | 60.12 | 27.82 |
| B20849 | No elastase | 60.13 | 24.57 |
| B20855 | No elastase | 60.81 | 22.08 |
| 40765 | No elastase | 63.69 | 28.42 |
| 24750 | No elastase | 60.22 | 24.71 |
| B20747 | Elastase | 60.92 | 28.95 |
| B20749 | Elastase | 62.01 | 26.43 |
| B20752 | Elastase | 60.15 | 23.27 |
| B20753 | Elastase | 59.66 | 29.30 |
| B20759 | Elastase | 58.36 | 28.19 |

TABLE 6-continued

| Lot #. | Treatment | Onset Tm (° C.) | Enthalpy (J/gdw) |
|---|---|---|---|
| B20837 | Elastase | 60.72 | 24.17 |
| B20842 | Elastase | 60.41 | 24.84 |
| B20844 | Elastase | 61.25 | 29.07 |
| B20849 | Elastase | 60.48 | 31.49 |
| B20855 | Elastase | 60.46 | 27.34 |
| 40765 | Elastase | 62.69 | 47.23 |
| 24750 | Elastase | 62.26 | 35.62 |

Figure 9:
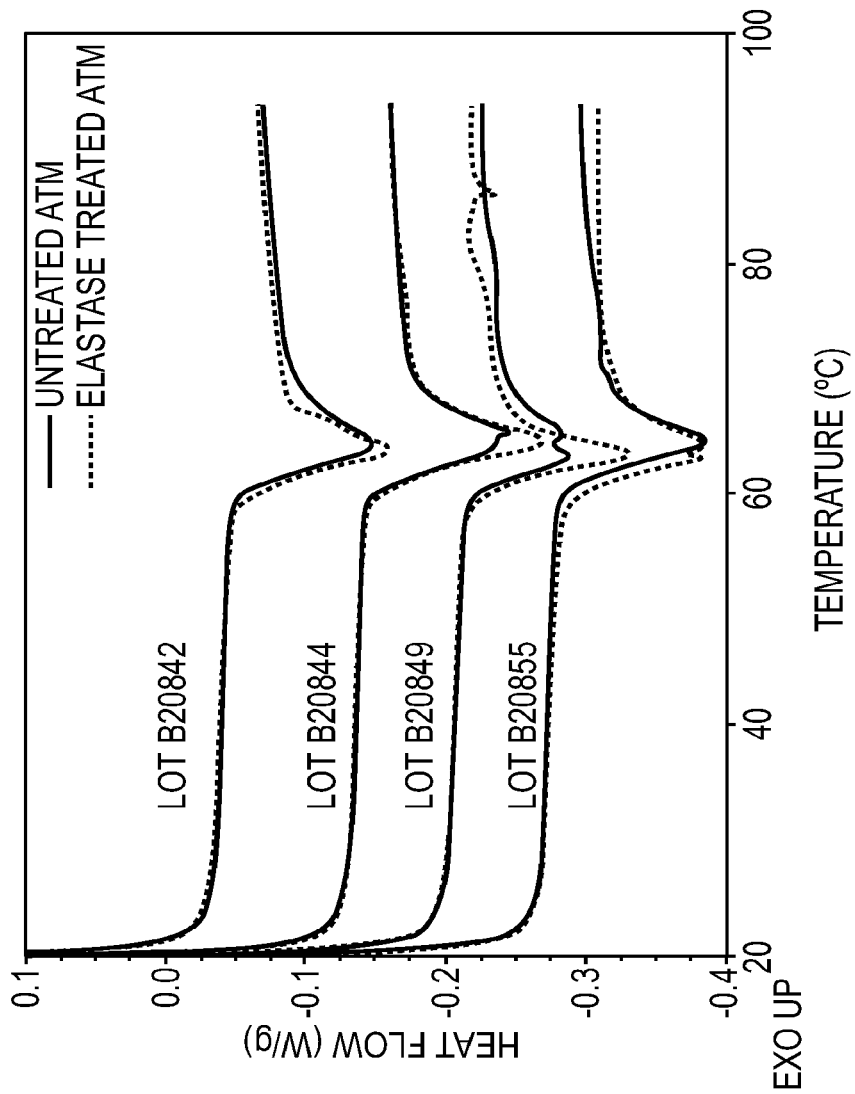
FIG. 9 is a line graph showing heat flow vs. temperature for untreated and elastase-treated tissue samples.

FIG. 9 is a graph that shows examples of DSC thermograms for paired samples of non-elastase-treated tissue samples (solid lines) and elastase-treated tissue samples (dashed lines). The graph shows temperature, in degrees Celsius ("° C.") on its abscissa (x-axis) and heat flow in Watts per gram ("W/g") on its ordinate (y-axis).

In the illustrated graph, data corresponding to paired tissue samples from four respective donor lots is shown. For each pair of tissue samples, the data suggests that elastase treatment has a minimal effect on a tissue sample's thermal response.

In general, DSC measures the thermochemical properties of tissue matrix. When collagen is heated to a certain temperature, its heat-labile intramolecular cross-links are broken, and the protein undergoes a transition from a highly organized crystalline structure to a random gel-like state. That may be referred to as denaturation. DSC thermograms give information about the structure of the matrix and its stability. For example, if tissue is gamma irradiated for sterilization, the onset denaturation temperature may be lowered due to gamma damage of the tissue. On the other hand, cross-linking typically increases the onset denaturation temperature.

Effect of Elastase Treatment on Susceptibility to Enzyme Degradation

The effect of elastase treatment on a tissue sample's susceptibility to enzyme degradation was considered.

Example 14

The effect of elastase treatment on a tissue sample's susceptibility to collagenase degradation was considered. Paired tissue samples from fifteen (15) different donor lots were tested. Each paired sample included one tissue sample that had been subjected to elastase treatment and one tissue sample that had not been subjected to elastase treatment. All of the tissue samples had been subjected to freeze drying with cryoprotectant after elastase treatment. The testing included exposing the tissue samples to collagenase for approximately six (6) hours. Table 7 includes results of the testing. More particularly, the table shows the percent of tissue remaining after collagenase exposure ("tissue remaining (%)").

Each row in Table 7 corresponds to a particular one of the tested tissue samples. The first column of the illustrated table identifies the donor lot number from which the corresponding tissue sample came. The second column identifies whether the corresponding tissue sample was exposed to elastase treatment. The designation "no elastase" means that the corresponding tissue sample was not exposed to elastase treatment. The designation "elastase" indicates that the corresponding tissue sample was exposed to elastase treatment. The first fifteen rows of data correspond to tissue samples that were not exposed to elastase treatment. The last fifteen rows of data correspond to tissue samples that were exposed to elastase treatment. The third column shows the percent of tissue that remained after exposure to the collagenase.

The first fifteen rows of data in the table correspond to the same respective donor lot numbers as the last fifteen rows of data in the table.

The data in the table shows that the elastase-treated tissue samples were slightly more susceptible to collagenase degradation than the non-elastase-treated tissue samples. On average, approximately 40.5% of the non-elastase-treated tissue samples remained after collagenase degradation, while, on average, approximately 34.2% of the elastase-treated tissue samples remained after collagenase degradation. Thus, elastase-treated ATM would likely be only slightly more susceptible to collagen degradation in vivo than elastase-treated ATM.

TABLE 7

| Lot #. | Treatment | Tissue Remaining (%) |
|---|---|---|
| B20747 | No elastase | 55.6% ± 1.1% |
| B20749 | No elastase | 82.6% ± 3.1% |
| B20752 | No elastase | 43.5% ± 4.3% |
| B20753 | No elastase | 37.7% ± 4.8% |
| B20759 | No elastase | 46.9% ± 4.6% |
| B20837 | No elastase | 49.7% ± 1.6% |
| B20842 | No elastase | 48.5% ± 3.0% |
| B20844 | No elastase | 44.3% ± 4.6% |
| B20849 | No elastase | 16.3% ± 4.7% |
| B20855 | No elastase | 50.7% ± 10.4% |
| B20908 | No elastase | 37.2% ± 2.7% |
| B20900 | No elastase | 13.7% ± 13.0% |
| B20911 | No elastase | 17.9% ± 2.1% |
| B20914 | No elastase | 29.7% ± 2.8% |
| B20915 | No elastase | 32.8% ± 2.6% |
| B20747 | Elastase | 35.3% ± 3.1% |
| B20749 | Elastase | 61.2% ± 5.5% |
| B20752 | Elastase | 47.0% ± 1.3% |
| B20753 | Elastase | 31.3% ± 4.8% |
| B20759 | Elastase | 36.2% ± 7.6% |
| B20837 | Elastase | 45.9% ± 1.9% |
| B20842 | Elastase | 34.2% ± 0.9% |
| B20844 | Elastase | 34.5% ± 3.4% |
| B20849 | Elastase | 7.4% ± 1.2% |
| B20855 | Elastase | 47.1% ± 5.3% |
| B20908 | Elastase | 41.1% ± 4.9% |
| B20900 | Elastase | 7.1% ± 3.1% |
| B20911 | Elastase | 15.2% ± 4.8% |
| B20914 | Elastase | 44.6% ± 7.8% |
| B20915 | Elastase | 25.1% ± 4.5% |

Example 15

The effect of elastase treatment on a tissue sample's susceptibility to trypsin degradation also was considered. Again, paired tissue samples from fifteen (15) different donor lots were tested. Each paired sample included one tissue sample that had been subjected to elastase treatment and one tissue sample that had not been subjected to elastase treatment. All of the tissue samples had been subjected to freeze drying with cryoprotectant. The testing included exposing the tissue samples to trypsin for a set period of time. Table 8 includes results of the testing. More particularly, the table shows the percent of tissue remaining after trypsin exposure ("tissue remaining (%)").

Each row in the illustrated table corresponds to a particular one of the tested tissue samples. The first column of the illustrated table identifies the donor lot number from which the corresponding tissue sample came. The second column identifies whether the corresponding tissue sample was exposed to elastase treatment. The designation "no elastase"

means that the corresponding tissue sample was not exposed to elastase treatment. The designation "elastase" indicates that the corresponding tissue sample was exposed to elastase treatment. The third column shows the percent of tissue that remained after exposure to trypsin.

The first fifteen rows of data in Table 8 correspond to the same respective donor lot numbers as the last fifteen rows of data in the table. The first fifteen rows of data correspond to tissue samples that were not exposed to elastase treatment. The last fifteen rows of data correspond to tissue samples that were exposed to elastase treatment.

The data in Table 8 shows that elastase treatment has very little effect on a tissue sample's susceptibility to trypsin degradation.

TABLE 8

| Lot | Treatment | Tissue remaining (%) |
| --- | --- | --- |
| B20747 | No elastase | 83.8% ± 1.7% |
| B20749 | No elastase | 92.0% ± 2.1% |
| B20752 | No elastase | 85.2% ± 0.8% |
| B20753 | No elastase | 85.1% ± 6.1% |
| B20759 | No elastase | 83.5% ± 1.3% |
| B20837 | No elastase | 89.1% ± 1.6% |
| B20842 | No elastase | 87.9% ± 3.6% |
| B20844 | No elastase | 82.2% ± 3.6% |
| B20849 | No elastase | 76.4% ± 2.2% |
| B20855 | No elastase | 85.5% ± 2.4% |
| B20908 | No elastase | 81.7% ± 0.4% |
| B20900 | No elastase | 76.9% ± 1.6% |
| B20911 | No elastase | 56.2% ± 1.9% |
| B20914 | No elastase | 58.9% ± 19.4% |
| B20915 | No elastase | 83.8% ± 0.9% |
| B20747 | Elastase | 93.0% ± 7.3% |
| B20749 | Elastase | 90.7% ± 4.4% |
| B20752 | Elastase | 84.0% ± 2.0% |
| B20753 | Elastase | 82.7% ± 2.9% |
| B20759 | Elastase | 80.0% ± 3.0% |
| B20837 | Elastase | 83.6% ± 2.8% |
| B20842 | Elastase | 87.7% ± 2.4% |
| B20844 | Elastase | 86.3% ± 2.8% |
| B20849 | Elastase | 80.6% ± 3.0% |
| B20855 | Elastase | 83.4% ± 1.1% |
| B20908 | Elastase | 83.1% ± 3.7% |
| B20900 | Elastase | 76.7% ± 5.8% |
| B20911 | Elastase | 64.7% ± 10.5% |
| B20914 | Elastase | 72.2% ± 0.9% |
| B20915 | Elastase | 77.3% ± 2.6% |

Tissue's Reaction to Elastase Treatment Over Time

Another experiment was conducted to consider a tissue sample's reaction to elastase treatment over time.

Example 16

In this experiment, tissue samples from two tissue donor lots were processed in accordance with LifeCell's proprietary methodology, discussed above, up to the tissue wash (step (iii)). The tissue was then cut into a number of 3 centimeter by 7 centimeter pieces. Some of those pieces were rinsed with Tris-HC1 buffer and treated with elastase. Then, changes in dimensions of the tissue samples were measured every three hours over a thirty-hour time span. Elastase was present throughout the entire time span. Dimensions of corresponding tissue samples that had not been treated with elastase also were measured. These dimensions are identified in FIGS. 10A and 10B as "control" measurements.

Figure 10A:
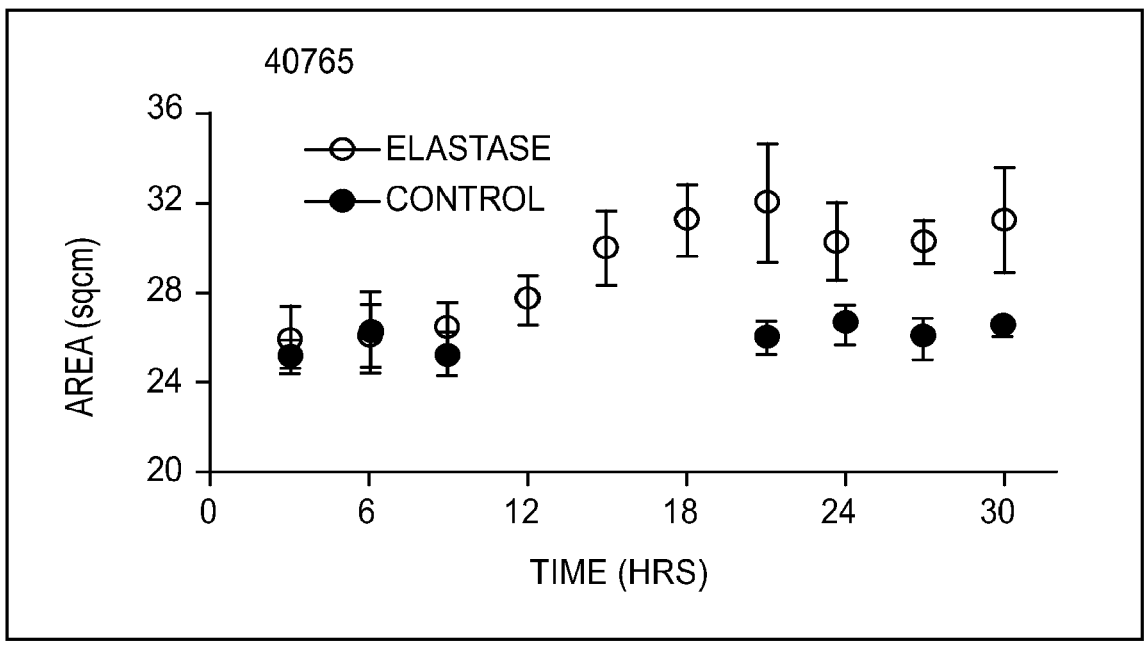
FIGS. 10A and 10B are graphs showing area changes of two tissue samples undergoing elastase treatment over time.
Figure 10B:
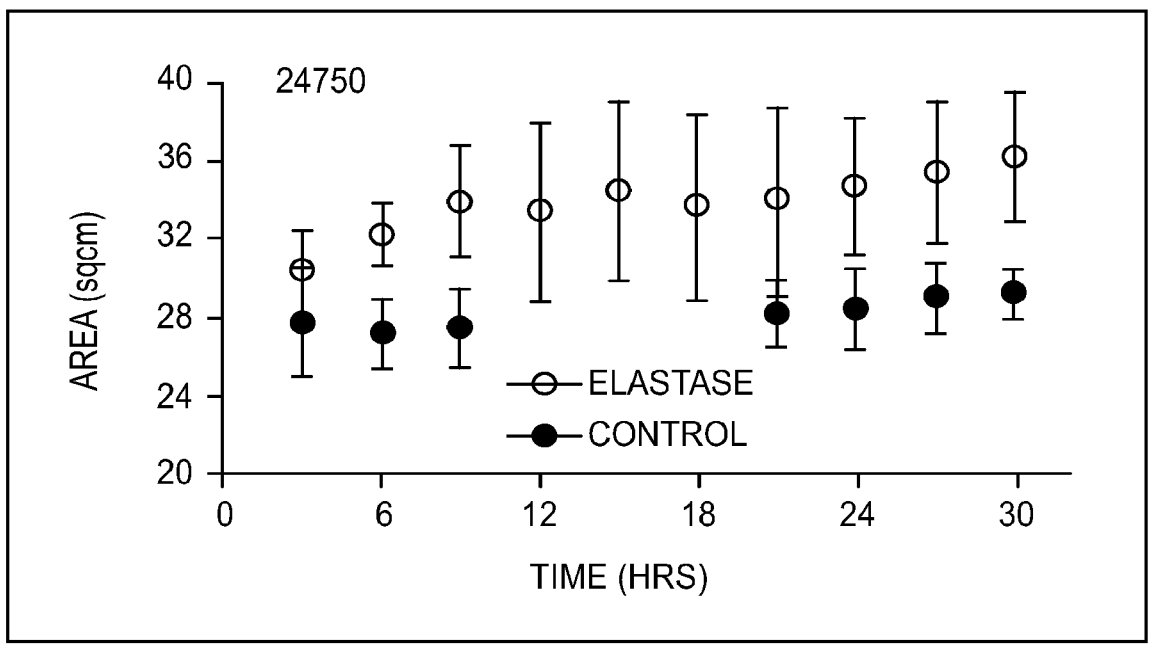

The graphs in FIGS. 10A and 10B show the results of this testing on tissue samples from two donor lots. The abscissas of the graphs correspond to time and the ordinates corresponds to area of a surface of the tissue samples. The graphs include data that corresponds to area of elastase-treated tissue samples (indicated by unshaded circles) and area of non-elastase-treated tissue samples (indicated by shaded circles) over a course of thirty hours.

FIG. 10A indicates that the elastase untreated tissue samples did not experience a significant change in area over the thirty hour period. The elastase-treated tissue samples, however, clearly experienced an increase in surface area over the thirty hour period. The most noticeable increase occurred between about hour 9 and hour 21. Thereafter, little change occurred in size of the elastase-treated tissue samples.

FIG. 10B also indicates that the elastase untreated tissue samples did not experience a significant change in area over the thirty hour period. The elastase-treated tissue samples, however, clearly experienced an increase in surface area over the thirty hour period. The most noticeable increase occurred between about hour 3 and hour 15. Thereafter, little change occurred in size of the elastase-treated tissue samples. In both FIGS. 10A and 10B, the tissue samples experienced very little growth after about 18 hours. After elastase treatment the tissue samples were rinsed with a tissue wash solution, no subsequent dimensional changes were observed.

A number of embodiments of the present disclosure have been described. Nevertheless, it will be understood that various modifications may be made without departing from the spirit and scope of the present disclosure.

For example, various types of tissue may be treated with elastase. The uses of elastase-treated tissues may be more expansive than those outlined herein. The elastase may be mixed with a variety of other substances to form a solution that is applied to the tissues. The tissues may be treated by soaking in elastase solution, having solution poured over it, being coated with elastase solution or by using any other method. Elastase may be selectively placed on certain areas of a tissue. Grafts or tissue implants may be implemented using multiple tissue pieces, one or more of which having been treated with elastase and one or more of which having been left untreated. Timing, concentrations, degree of agitation, ambient temperature and pressure conditions all may be varied considerably.

Accordingly, other implementations are within the scope of the following claims.

The invention claimed is:

1. A modified acellular tissue matrix (mATM), comprising:
   a dermal acellular tissue matrix including a collagen network and a disrupted elastin network, wherein the mATM extends between about 14% and 24% under an applied tensile force of about 5 newtons/cm.

2. The mATM of claim 1, wherein the collagen network is substantially intact.

3. The mATM of claim 1, wherein the collagen network does not include cross-linking.

4. The mATM of claim 1, wherein the collagen network has substantially similar histological, thermal, and material properties as a collagen network in an acellular tissue matrix with an undisrupted elastin network.

5. The mATM of claim 1, wherein the dermal acellular tissue matrix is a porcine tissue matrix.

6. The mATM of claim 1, wherein the dermal acellular tissue matrix is a human tissue matrix.

7. The mATM of claim 1, wherein the dermal acellular tissue matrix is a bovine tissue matrix.

8. The mATM of claim 1, wherein the disrupted elastin network is disrupted by a solution with a concentration of elastase over an exposure time.

9. The mATM of claim 8, wherein the concentration of elastase ranges from about 0.1 units/milliliter to 0.5 units/milliliter.

10. The mATM of claim 9, wherein the concentration of elastase ranges from about 0.2 units/milliliter to 0.25 units/milliliter.

11. The mATM of claim 8, wherein the exposure time ranges from about 12 hours to 24 hours.

12. The mATM of claim 11, wherein the exposure time ranges from 18 hours to 24 hours.

13. The mATM of claim 1, wherein the dermal acellular tissue matrix is in a form of a sheet.

14. The mATM of claim 1, wherein the collagen network is substantially intact and the elastin network is disrupted to produce a dermal matrix with reduced initial stretchability compared to dermal matrices with intact elastin.

15. A method comprising:
    providing the mATM of claim 1;
    identifying a vertebrate subject as having an organ or tissue in need of treatment; and
    placing the mATM in or on the tissue or organ.

* * * * *